United States Patent
Martucci et al.

(10) Patent No.: US 11,696,720 B2
(45) Date of Patent: *Jul. 11, 2023

(54) PROCESSOR IMPLEMENTED SYSTEMS AND METHODS FOR MEASURING COGNITIVE ABILITIES

(71) Applicant: Akili Interactive Labs, Inc., Boston, MA (US)

(72) Inventors: Walter E. Martucci, Boston, MA (US); Adam Piper, Boston, MA (US); Matthew Omernick, Boston, MA (US); Adam Gazzaley, Boston, MA (US); Eric Elenko, Boston, MA (US); Jeffery Bower, Boston, MA (US); Scott Kellogg, Boston, MA (US); Ashley Mateus, Boston, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/480,778

(22) Filed: Sep. 21, 2021

(65) Prior Publication Data

US 2022/0117528 A1 Apr. 21, 2022

Related U.S. Application Data

(63) Continuation of application No. 15/068,061, filed on Mar. 11, 2016, now Pat. No. 11,122,998.

(Continued)

(51) Int. Cl.
*A61B 5/16* (2006.01)
*A61B 5/00* (2006.01)
(Continued)

(52) U.S. Cl.
CPC ............ *A61B 5/4088* (2013.01); *A61B 5/162* (2013.01); *A61B 5/4833* (2013.01); *G09B 7/00* (2013.01);
(Continued)

(58) Field of Classification Search
CPC ..... A61B 5/162; A61B 5/4088; A61B 5/4833; A61B 5/7267; A61B 2562/0219; G09B 7/00; G16H 50/20
See application file for complete search history.

(56) References Cited

U.S. PATENT DOCUMENTS 6,053,737 A * 4/2000 Babbitt .................... G09B 9/08
434/30
8,078,253 B2 * 12/2011 Teicher .................. G16Z 99/00
600/407

(Continued)

FOREIGN PATENT DOCUMENTS

WO WO-2012064999 A1 * 5/2012 ............. A61B 5/162

*Primary Examiner* — Jack Yip
(74) *Attorney, Agent, or Firm* — Gregory Finch; Finch Paolino, LLC

(57) ABSTRACT

A computer-implemented cognitive assessment tool is provided for assessing cognitive ability of an individual while multi-tasking. In one embodiment, a computer processing system on which the tool is implemented may receive form the individual first responses to a first task and second responses to a second task, where the first task and the second task are presented to the individual simultaneously. The system may determine that the first task and the second task are performed by the individual based on the first responses and the second responses, and compute a cognitive measure using one or both of the first responses and the second responses. Further, computing the cognitive measure may be based on performance measures of one or both of the first responses and the second responses. Based on the (Continued)

cognitive measure, the system may output a cognitive assessment to the individual.

20 Claims, 6 Drawing Sheets

Related U.S. Application Data

(60) Provisional application No. 62/132,009, filed on Mar. 12, 2015.

(51) Int. Cl.
*G09B 7/00* (2006.01)
*G16H 50/20* (2018.01)

(52) U.S. Cl.
CPC ............ *G16H 50/20* (2018.01); *A61B 5/7267* (2013.01); *A61B 2562/0219* (2013.01)

(56) References Cited

U.S. PATENT DOCUMENTS

| | | | |
|---|---|---|---|
| 9,308,445 B1* | 4/2016 | Merzenich | A63F 13/537 |
| 2006/0161218 A1* | 7/2006 | Danilov | A61B 5/682 |
| | | | 607/45 |
| 2007/0077204 A1* | 4/2007 | Devanand | A61K 49/00 |
| | | | 424/9.2 |
| 2008/0167571 A1* | 7/2008 | Gevins | A61B 5/377 |
| | | | 600/544 |
| 2010/0041001 A1* | 2/2010 | Delahunt | G09B 7/00 |
| | | | 434/236 |
| 2010/0292545 A1* | 11/2010 | Berka | A61B 5/374 |
| | | | 600/301 |
| 2012/0088222 A1* | 4/2012 | Considine | G09B 5/00 |
| | | | 434/362 |
| 2012/0108997 A1* | 5/2012 | Guan | A61B 5/374 |
| | | | 600/545 |
| 2012/0271194 A1* | 10/2012 | MacLullich | A61B 5/16 |
| | | | 600/558 |
| 2013/0216986 A1* | 8/2013 | Goldman | G09B 7/00 |
| | | | 434/236 |
| 2013/0345524 A1* | 12/2013 | Meyer | A61B 5/7455 |
| | | | 434/362 |
| 2014/0207292 A1* | 7/2014 | Ramagem | G05D 23/1902 |
| | | | 700/278 |
| 2014/0370479 A1* | 12/2014 | Gazzaley | A61B 5/168 |
| | | | 434/322 |
| 2015/0004577 A1* | 1/2015 | Wu | G09B 19/00 |
| | | | 434/236 |
| 2016/0022167 A1* | 1/2016 | Simon | A61B 5/4064 |
| | | | 600/301 |
| 2016/0089089 A1* | 3/2016 | Kakkar | G16H 40/67 |
| | | | 600/484 |
| 2016/0349274 A1* | 12/2016 | Williams | G01N 33/6896 |

* cited by examiner

PROCESSOR IMPLEMENTED SYSTEMS AND METHODS FOR MEASURING COGNITIVE ABILITIES

CROSS-REFERENCE TO RELATED APPLICATIONS

This application is a continuation of U.S. application Ser. No. 15/068,061 filed Mar. 11, 2016, which claims the benefit of U.S. Provisional Application No. 62/132,009 filed Mar. 12, 2015; the entirety of each of these applications are hereby incorporated herein by reference.

FIELD

The disclosed embodiments generally relates to a computer-implemented methods for measuring cognitive function of an individual.

BACKGROUND

Cognitive function is recognized as an informative marker of many disease processes such as dementia, depression, Autism Spectrum Disorder, Attention Deficit Hyperactivity Disorder, and even healthy aging. For this reason, monitoring cognitive function has become an important part of an individual's screening, medical diagnosis, monitoring of therapy, and investigation into the emerging cognitive training field.

SUMMARY

Conventional validated cognitive assessment tools have a few problems.

The primary issue is that the cognitive assessment process are tedious for a user to perform. The un-engaging tasks and interface do not create the environment in which every user performs to his or her highest abilities, consequently giving inaccurate scores and normative data sets. Additionally, users may be unwilling to comply with a request to perform the same assessment process multiple times.

The second issue with current cognitive assessment processes is that they can be time consuming for both the user and the person evaluating the user's performance. In some cases this leads to the decision to not undergo cognitive evaluation, even though the information provided could be of value. It also makes it logistically difficult to perform the same cognitive evaluation on one person many times to understand how his or her cognitive function is changing over time.

Finally, currently available cognitive assessments are insensitive to known cognitive deficits in populations. It is to be appreciated that there is no known currently available and commonly used cognitive tools capable of distinguishing a population with chromosomal abnormality in 16p.11.2 BP4-BP5 that causes behavioral and cognitive symptoms from a group of age-matched siblings.

Thus, a new cognitive assessment tool would be useful if it could detect deficits that are not optimally identified by current tools and are engaging or seamlessly incorporated into everyday tasks. This present disclosure describes a unique computer-implemented cognitive assessment tool that evaluates user inputs when a user is performing at least two tasks simultaneously. This new tool may be enabled by computers because computers allow two tasks to be presented, adapted, and evaluated simultaneously, which is something humans cannot achieve with fidelity and reliability. The methods of this disclosure can be used in medical, educational, and professional settings. The cognitive assessment tool described below can be used as a one-time evaluation or given to two or more times for monitoring purpose without significant strain on the user or the person evaluating the cognitive function.

The purpose and advantages of the below described illustrated embodiments will be set forth in and apparent from the description that follows. Additional advantages of the illustrated embodiments will be realized and attained by the devices, systems and methods particularly pointed out in the written description and claims hereof, as well as from the appended drawings.

Measuring and understanding cognitive function is important in many areas: diagnosing a disease, diagnosing a neurological condition, monitoring response to and side effects of medical interventions, and addressing educational placements and needs. However, current cognitive measurement tools are either too time consuming to be performed on a regular basis, have poor compliance and adherence because they do not keep the user engaged, or can be insensitive to known differences in cognitively impaired populations. The present disclosure provides a novel cognitive assessment that measures performance through user inputs to a computer device while the user is performing at least two tasks at once ("multi-tasking").

While other cognitive assessments may rely on user inputs to computational devices, most rely on a participant performing only one task at a time, or having a second task be present but not meant to be performed (for example, a distraction to be ignored). The existing cognitive assessment method that does incorporate multi-tasking specifically focuses the method on highlighting the difference between the multi-tasking phase versus separate performance of the single-task components in isolation, and finds that the utility of the method lies solely in calculating the performance cost of being in a multi-tasking environment by comparing the multi-task performance to when the task is performed by itself. A unique aspect of the present disclosure is that it finds that performance data collected in the multi-tasking environment, in addition to the previously useful multi-tasking "cost" data, can be specifically informative of a user's cognitive state and in some cases more sensitive than the cost data.

The methods described are implemented on a computer device with an input component. The computer device enables the methods because it allows for the presentation of two tasks and measurement of user responses to the two tasks simultaneously, which is something humans are not capable of doing with fidelity and reliability. The computer device also allow for the adaption of difficulty of both tasks independently. Additionally, without the temporal resolution that the computer device is able to provide, the performance measurements would be not be effective cognitive measures.

The present disclosure describes computer-implemented methods for measuring cognitive ability or function of an individual, wherein the method may be implemented using a computer device having an input component. Measurements may be taken while the user is performing at least two distinct tasks ("multi-tasking"), each of which requiring an input to the computer device. The computer may perform an analysis of the performance measures of at least one of the tasks based on a cognitive measure, and based on the cognitive measure output an assessment indicative of cognitive ability or function of the user.

This method can be implemented in multiple scenarios, including measurement of performance when the user engages in two or more tasks simultaneously for purposes other than cognitive measurement (passive tasks) and active measurement of performance on prescribed tasks specifically designed for cognitive assessment (active tasks). Examples of passive tasks are: writing emails, responding to instant messages, and browsing the internet. Active tasks are those that are designed to evaluate a user's cognitive function in a specific domain, such as memory task. Commercially available video games often engage users in multi-tasking and offer an excellent opportunity for cognitive evaluation. Additionally, video games may be specifically designed to present multi-tasking with active tasks.

In one aspect, the user inputs in a multi-task environment may be analyzed based on different performance measures. Among them are the performance threshold for which a certain accuracy can be maintained, the mean performance over a period of time, the variation in the performance level over time, the reaction time to certain stimuli, the variation in the reaction time, and the ability to differentiate between interference stimuli to which a user should respond and distractor stimuli which should be ignored. These performance measures can be analyzed using standard techniques, combined to create composite variables, and measured over time to provide additional cognitive measures.

The methods of this disclosure can be used, among other things, to diagnose cognitive deficits, to help diagnose specific disease states, to monitor response to a therapy, to monitor for side effects in therapies known to cause cognitive side effects or those with unknown pharmacodynamics, and to help in educational assessments and placements.

In the described illustrated embodiments, presented are specific embodiments of the deployment, testing, and efficacy of this new approach in various clinical populations. In some illustrated embodiments, the computer-based cognitive assessment tools are implemented in a video game that presents two active cognitive tasks simultaneously. In a few particularly illustrated embodiments, the computer-based methods are implemented in a video game that presents a visuomotor task and a perceptual reaction task simultaneously. The illustrated embodiment can be tested to show known cognitive decline in aging populations, differentiate between populations with more accuracy than traditional cognitive measures, differentiation between different clinical populations, and show stability of the tool's measurements over time.

For example, the present disclosure provides various exemplary embodiments of the cognitive assessment tool described above. In one embodiments, the computer-implemented method for assessing cognitive ability of an individual is implemented using a hand-held computing device having a display component, an input device, and a sensor. The method comprises: presenting, by the display component, a visuomotor task to the individual over a period of time, the visuomotor task including a navigation path evoking navigation responses from the individual; presenting, by the display component, a reaction task to the individual over the period of time, the reaction task including target stimuli evoking reaction responses from the individual and distractor stimuli that require no response from the individual, wherein the stimuli are presented simultaneously with at least some of the navigation path; receiving the navigation responses using the sensor; receiving the reaction responses using the input device; determining, by the hand-held computing device, that the visuomotor task is being performed by the individual based on the navigation responses; computing, by the hand-held computing device, a cognitive measure using the reaction responses; outputting, by the hand-held computing device, a cognitive assessment based on the cognitive measure.

In one embodiment, the present disclosure provides a computer-implemented method for assessing cognitive ability of an individual. In one embodiment, the computer-implemented method comprises: receiving, by a computer processing system, a first plurality responses by the individual to a first task, the first task including first stimuli evoking the first plurality of responses from the individual over a period of time; receiving, by the computer processing system, a second plurality of responses by the individual to a second task, the second task including second stimuli evoking the second plurality of responses from the individual over the period of time, wherein the second stimuli are presented simultaneously with at least some of the first stimuli; determining, by the computer processing system, that the first task and the second task are performed by the individual based on the first plurality of responses and the second plurality of responses; computing, by the computer processing system, a cognitive measure using one or both of the first plurality of responses and the second plurality of responses; and outputting, by the computer processing system, a cognitive assessment based on the cognitive measure.

In related examples of embodiments, computing the cognitive measure includes determining performance measures using one or both of the first plurality of responses and the second plurality of responses.

In related examples of embodiments, the performance measures are selected from the group consisting of: reaction time of responses and correctness of responses.

In related examples of embodiments, one or both of the first plurality of responses and the second plurality of responses are detected using one or more sensors, the sensors being selected from the group consisting of: accelerometer and gyroscope.

In related examples of embodiments, the computer-implemented method can further include the steps of: determining performance measures using one or both of the first plurality of responses and the second plurality of responses; and modifying, during the period of time, a difficulty level of the first task or the second task based on performance measures.

In related examples of embodiments, the difficulty level corresponds to a game level.

In related examples of embodiments, the difficulty level is selected from the group consisting of: allowable reaction time window for reacting to stimuli, navigation speed, number of obstacles, size of obstacles, frequency of turns in a navigation path, and turning radiuses of turns in a navigation path.

In related examples of embodiments, the difficulty level is modified in real-time during the period of time; and wherein the cognitive measure is computed using the difficulty level modifications made during the period of time.

In related examples of embodiments, the computer-implemented method can further include the steps of: determining a threshold of the difficulty level at which the performance measures satisfy one or more predetermined criteria; wherein the cognitive measure is computed using the determined threshold of the difficulty level.

In related examples of embodiments, the one or more predetermined criteria include maintaining a predetermined level of performance over a predetermined amount of time.

In related examples of embodiments, the computer-implemented method can further include the steps of: modifying, during the period of time, a first difficulty level of the first task based on performance measures of one or both of the first plurality of responses and the second plurality of responses; and modifying, during the period of time, a second difficulty level of the second task based on performance measures of one or both of the first plurality of responses and the second plurality of responses; wherein the first difficulty level and the second difficulty level are modified in real-time during the period of time; and wherein the cognitive measure is computed using one or both of the first difficulty level modifications and the second difficulty level modifications.

In related examples of embodiments, the first task is a visuomotor task, the first stimuli include a navigation path, and the first plurality of responses include continuous inputs.

In related examples of embodiments, the second task is a reaction task, the second stimuli include target stimuli that require responses from the individual, and the second plurality of responses include inputs reacting to the interferences.

In related examples of embodiments, the second stimuli include distractor stimuli that require no response from the individual.

In related examples of embodiments, computing the cognitive measure includes applying statistical analysis to one or both of the first plurality of responses and the second plurality of responses.

In related examples of embodiments, computing the cognitive measure includes comparing the performance measures to predetermined performance measures representative of individuals with known cognitive conditions.

In related examples of embodiments, computing the cognitive measure includes applying a computer data model to the performance measures.

In related examples of embodiments, the computer data model is trained based on performance measures of individuals with known cognitive conditions.

In related examples of embodiments, the computer data model is trained using a technique selected from the group consisting of: machine learning, pattern recognition, regression analysis, and Monte Carlo technique.

In related examples of embodiments, computing the cognitive measure includes computing a hit rate, false alarm rate, correct response rate, or miss rate.

In related examples of embodiments, computing the cognitive measure includes applying a signal detection technique selected from the group consisting: sensitivity index, receiver operating characteristics (ROC), and bias.

In related examples of embodiments, the cognitive measure is a composite measure computed using performance measures of the first plurality of responses to the first task and performance measures of the second plurality responses to the second task.

In related examples of embodiments, the cognitive measure is a composite measure computed using at least two types of performance measures of one of the first plurality of responses and the second plurality of responses.

In related examples of embodiments, the cognitive measure is a composite measure computed using non-performance information and performance measures of one or both of the first plurality of responses and the second plurality of responses.

In related examples of embodiments, non-performance information is selected from the group consisting of: demographic, age, gender, and health data of the individual.

In related examples of embodiments, the cognitive assessment provides a diagnosis of cognitive disorder.

In related examples of embodiments, the cognitive assessment is used to monitor the individual's cognitive ability over time.

In related examples of embodiments, the cognitive assessment is used to monitor an effect of therapy on the individual's cognitive ability.

In related examples of embodiments, the second stimuli are presented at exactly the same time with at least some of the first stimuli.

In related examples of embodiments, one of the second stimuli is presented with an associated first stimuli consecutively with a slight time differential.

The exemplary embodiments of computer-implemented methods described above may be implemented using a computer-implemented system comprising a one or more processors; and a memory comprising instructions which when executed cause the one or more processors to execute one or more steps described above. In one embodiment, the exemplary embodiments of computer-implemented methods described above may be implemented using a computer-implemented system comprising a hand-held computing device having one or more processors, a display component, an input device, and a sensor; and a memory comprising instructions which when executed cause the one or more processors to execute one or more steps described above.

The exemplary embodiments of computer-implemented methods described above may also be implemented as instructions encoded on a non-transitory computer-readable medium, the instructions being configured to cause a computer processing system to execute one or more steps described above. In one embodiment, the exemplary embodiments of computer-implemented methods described above may be implemented as instructions encoded on a non-transitory computer-readable medium, the instructions being configured to cause a hand-held computing device having a display component, an input device, and a sensor to execute one or more steps described above.

BRIEF DESCRIPTION OF THE DRAWINGS

The accompanying appendices and/or drawings illustrate various non-limiting, example, inventive aspects in accordance with the present disclosure.

DETAILED DESCRIPTION

Figure 1:
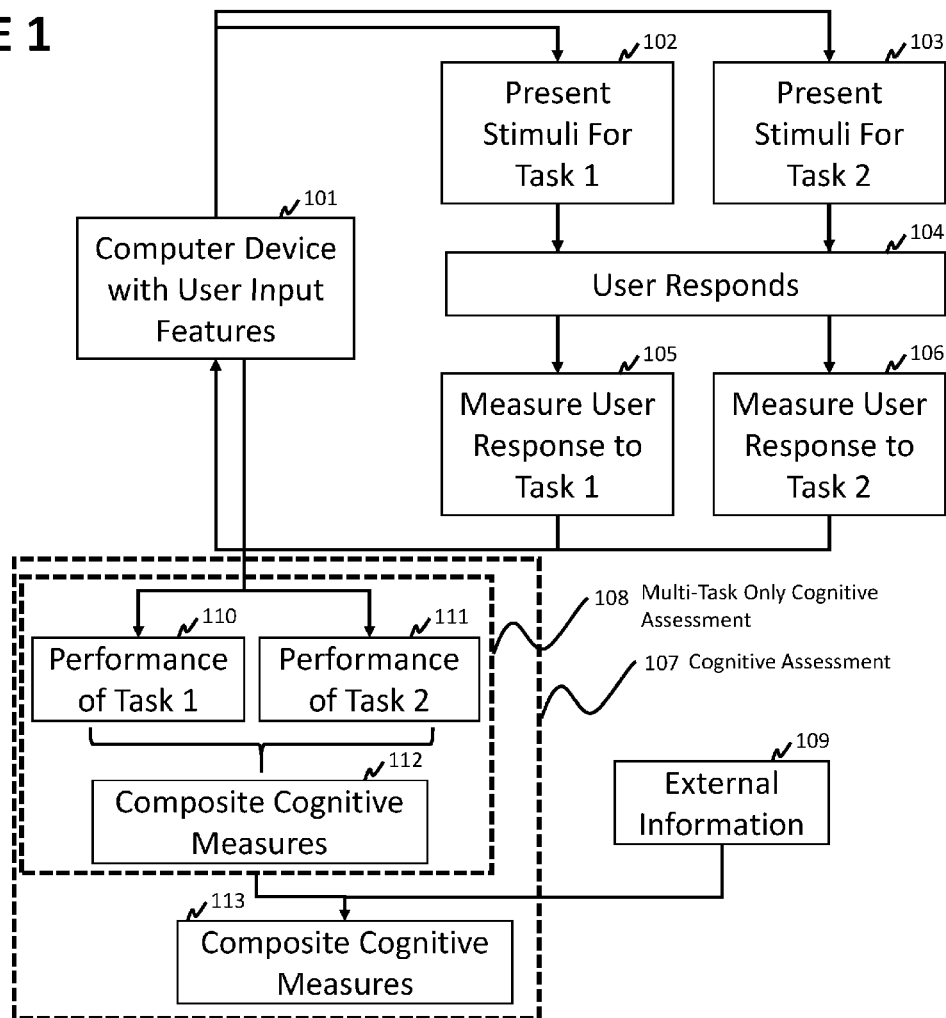
FIG. 1 is a flow diagram of an exemplary embodiment of the cognitive assessment tool.

The illustrated embodiments are now described more fully with reference to the accompanying drawings wherein like reference numerals identify similar structural/functional features. The illustrated embodiments are not limited in any way to what is illustrated as the illustrated embodiments described below are merely exemplary, which can be embodied in various forms, as appreciated by one skilled in the art. Therefore, it is to be understood that any structural and functional details disclosed herein are not to be interpreted as limiting, but merely as a basis for the claims and as a representation for teaching one skilled in the art to variously employ the discussed embodiments. Furthermore, the terms and phrases used herein are not intended to be limiting but rather to provide an understandable description of the illustrated embodiments.

Where a range of values is provided, it is understood that each intervening value, to the tenth of the unit of the lower limit unless the context clearly dictates otherwise, between the upper and lower limit of that range and any other stated or intervening value in that stated range is encompassed within the illustrated embodiments. The upper and lower limits of these smaller ranges may independently be included in the smaller ranges is also encompassed within the illustrated embodiments, subject to any specifically excluded limit in the stated range. Where the stated range includes one or both of the limits, ranges excluding either both of those included limits are also included in the illustrated embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the illustrated embodiments, exemplary methods and materials are now described. All publications mentioned herein are incorporated herein by reference to disclose and describe the methods and/or materials in connection with which the publications are cited.

When describing the methods and compositions of the present disclosure, the following terms include the following meanings unless otherwise indicated, but the terms are not to be understood to be limited to their accompanying meanings as rather it is to be understood to encompass any meaning in accordance with the teachings and disclosure of the present invention.

The term "cognitive measure" or "measure of cognitive ability or function," as used herein, may refer to a representation of the state of the user's mental processes of perception, memory, judgment, reasoning, and/or the like. In some embodiments, the representation can be for a specific type of function (e.g. memory). In some embodiments, the representation can be for several types of functions (e.g., memory and perception). In some embodiments, the representation can pertain to all of them as a whole.

The term "task," as used herein, may refer to any method or process of an individual responding to stimuli. In some embodiments, stimuli may be presented specifically to measure cognitive function, making it an "active task." In some embodiments, stimuli may be presented as part of routine computer device use and not specifically for cognitive function, making it a "passive task."

The term "simultaneous," as used herein, may refer to two or more things being in substantially the same time period (e.g., having no difference in time or a slight differential such as 0.1 second, 0.5 second, or 1 second). For example, in certain embodiments, two or more things are simultaneous if they both occur at the exact same time. In some embodiments, two or more things are simultaneous if they occur consecutively separated by a slight time differential. In some embodiments, two or more things are simultaneous if they occur on a rotating basis each for a short time period with no breaks in between. In some embodiments, two or more things are simultaneous if they are set for the same period of time.

The term "multi-tasking," as used herein, may refer to a user performing at least two tasks simultaneously. The tasks may be active or passive tasks.

The term "single-tasking," as used herein, may refer to a user performing only one task for a set period of time. The task may be an active or a passive task.

The term "game-level," as used herein, may refer to the discrete stimulus magnitude values associated with a specific task in a video game. Each level may correspond to a specific increment in a parameter related to task. Increasing levels may present increasingly difficult tasks.

The term "threshold," as used herein, may refer to the level of stimuli magnitude of a task that is the limit of a person to perform the task to a specified level of correctness based on one or more predetermined criteria.

The term "stimuli," as used herein, may refer to computer device presenting sensory events for the user that evoke a specific functional reaction. For example, a reaction may be an interaction with the computer device. In some embodiments, stimuli may include a navigation path through which the user is instructed to navigate. In some embodiments, stimuli may include interferences that distract the user from another task and evoke user response. In some embodiments, stimuli may include distracters that distract the user from another task and require no response from the user. In some embodiments, stimuli may include multiple types of stimuli with different response requirements.

The term "distractor stimuli," as used herein, may refer to a specific stimuli for a perceptual reaction task in which the user is not supposed to react to the stimuli or provide computer inputs. Providing inputs for a distractor stimuli is considered an incorrect response to the task which presents the stimuli. In some embodiments, non-responses may be considered a response to such distractor stimuli (e.g., a correct response to a distractor stimuli may be the absence of response within a time window).

The term "neurotypical," as used herein, may refer to a description of a person who has no known cognitive deficits.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

It is to be appreciated the illustrated embodiments discussed below are preferably a software algorithm, program or code residing on computer useable medium having control logic for enabling execution on a machine having a computer processor. The machine typically includes memory storage configured to provide output from execution of the computer algorithm or program.

As used herein, the term "software" is meant to be synonymous with any code or program that can be in a processor of a host computer, regardless of whether the implementation is in hardware, firmware or as a software computer product available on a disc, a memory storage device, or for download from a remote machine. The embodiments described herein include such software to implement the equations, relationships and algorithms described above. One skilled in the art will appreciate further features and advantages of the illustrated embodiments based on the above-described embodiments. Accordingly, the illustrated embodiments are not to be limited by what has been particularly shown and described, except as indicated by the appended claims. All publications and references cited herein are expressly incorporated herein by reference in their entirety.

FIG. 1 is a general flow diagram of an embodiment of the cognitive assessment tool as described herein. In one embodiment, the cognitive assessment tool may be implemented on a computer device with user input features 101. The computer device may simultaneously present stimuli of two tasks 102, 103 to the user. Tasks 102 and/or 103 may include task the user engages in voluntarily for purposes other than cognitive assessment or task assigned to the user 104 by a program for purposes of cognitive assessment. In a preferred embodiment, task 102 is a visuomotor task and task 103 is a perpetual reaction task. The user may then respond to both tasks 104 and those responses are detected or measured 105, 106 by the computer device 101 (e.g., the responses may be detected as mouse clicks, screen taps, accelerometer readings, etc.). The computer device 101 may analyze the user responses to the tasks 105, 106 and convert them into a cognitive assessment 107 that is representative of the user's cognitive ability or function. In some embodiments, the cognitive assessment 107 may be based on a performance measure of responses to one specific task (e.g., performance measure of task 1 110 or performance measure of task 2 111). In other embodiments, the cognitive assessment 107 may be a composite measures 112 based on performances measures of responses to one or both tasks (e.g., performance measures of task 1 110 and/or performance measures of task 2 111). In some embodiments, cognitive assessment 108 may be based only on measures 110, 111, and 112 of user inputs while multi-tasking. In some embodiments, cognitive assessment 107 may be based on composite measure 113 computed using additional external or non-performance information 109, such as the user's demographic information or normative data.

Figure 2:
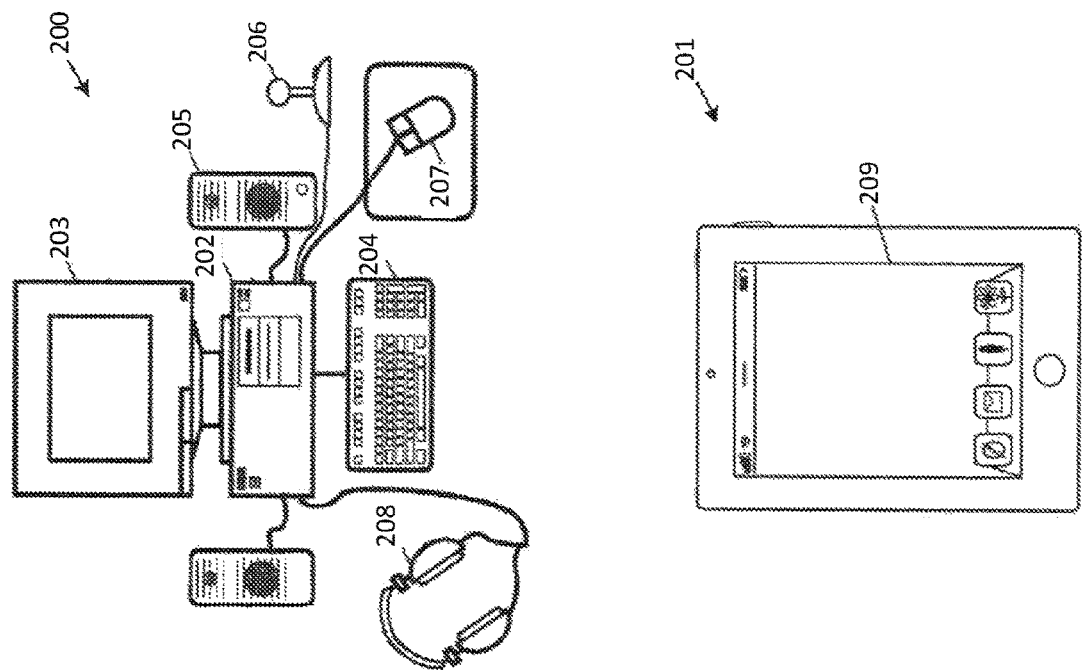
FIG. 2 illustrates examples of computer processing systems on which the cognitive assessment tool may operate.

FIG. 2 illustrates two types of computer processing systems 200 and 201 with which embodiments of the present disclosure may be practiced. In one embodiment, the computer system 200 may contain a computer 202, having a CPU, memory, hard disk and CD ROM drive (not shown), attached to a monitor 203. The monitor 203 provides visual prompting and feedback to the subject during execution of the computer program. Attached to the computer 202 are a keyboard 204, speakers 205, a joystick 206, a mouse 207, and headphones 208. In some embodiments, the speakers 205 and the headphones 208 may provide auditory prompting, stimuli, and feedback to the subject during execution of the computer program. The joystick 206 and mouse 207 allow the subject to navigate through the computer program, and to select particular responses after visual or auditory prompting by the computer program. The keyboard 204 allows the subject or an instructor to enter alphanumeric information about the subject into the computer 202. In alternative embodiments, the computer may incorporate additional input or output elements such as sensors to monitor physical state or the user or video camera technologies to monitor movement. The methods disclosed can be deployed on a number of different computer platforms e.g. IBM or Macintosh or other similar or compatible computer systems, gaming consults, or laptops.

FIG. 2 also illustrates a suitable mobile computing environment, for example, a tablet personal computer or a mobile telephone or smartphone 201 on which embodiments of the cognitive assessment tool may be deployed. In one embodiment, mobile computing device may be a handheld computer having both input elements and output elements. Input elements may include touch screen display 209, input buttons (not shown) that allow the user to enter information into the mobile computing device, and internal sensors, such as accelerometer and gyroscope measurement units (not shown), that allow the user to record movement of the device. The screen display 209 may provide visual prompting, stimuli, and feedback to the user during execution of the computer program. The output elements comprise the inbuilt speaker (not shown) that in some embodiments may provide auditory prompting, stimuli, and feedback to the user during execution of the computer program. In alternative embodiments, the mobile computing device may incorporate additional input or output elements such as a physical keypad to enter alphanumeric information, attachments with sensors to monitor physical state, or a headphone jack (not shown). Additionally, the mobile computing device may incorporate a vibration module (not shown) which causes mobile computing device to vibrate to provide stimulus or feedback to a user during execution of the computer program.

Figure 3:
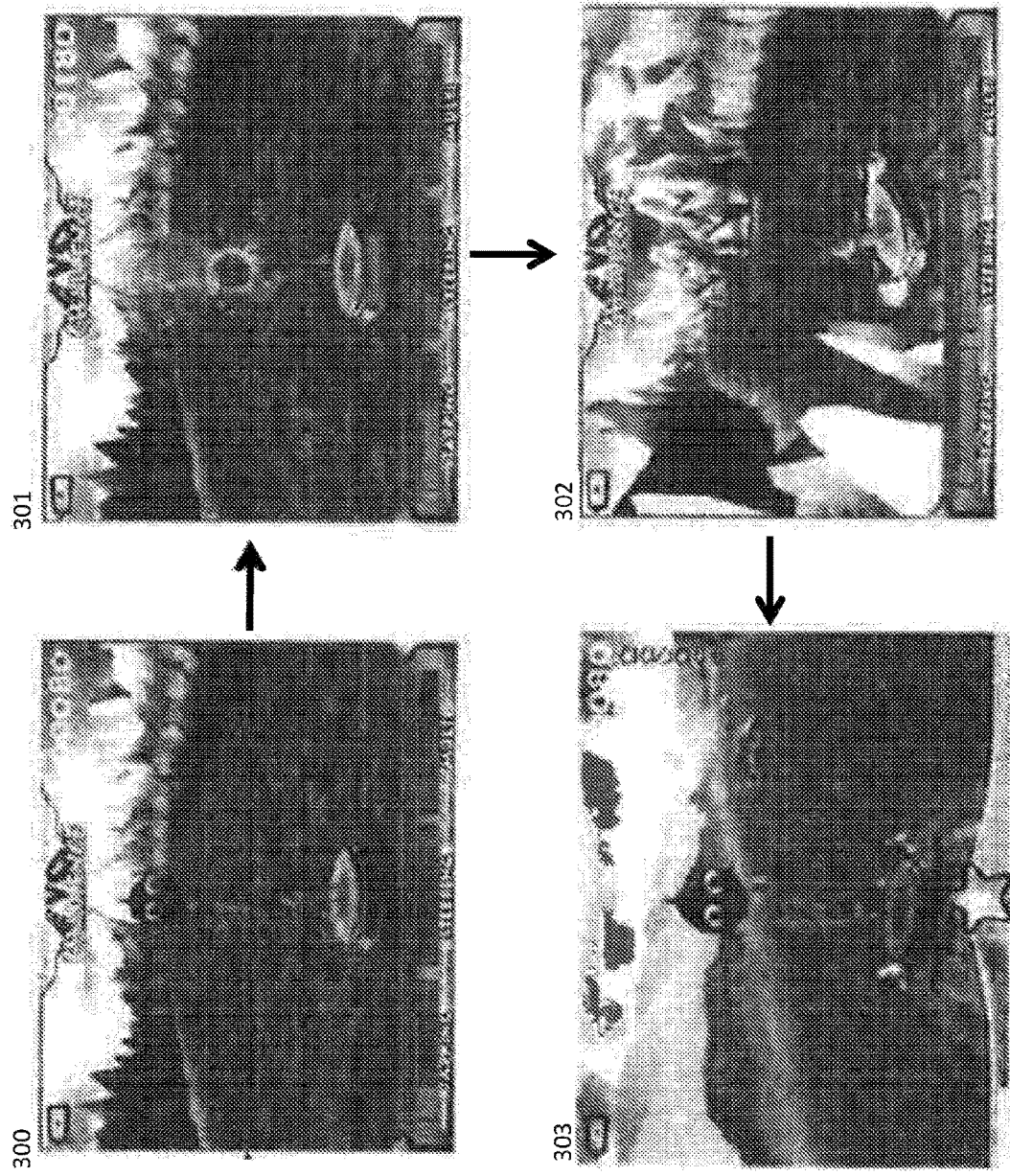
FIG. 3 depicts screen shots of an exemplary preferred embodiment of the cognitive assessment tool.

FIG. 3 are screen shots of a preferred embodiment of the disclosed methods, Project: EVO. Screen shot 300 shows an image of a target being presented for the perceptual reaction "Tapping" task. Screen shot 301 shows a target that the user has reacted too. The computer collects information on the user response. Screen shot 302 shows a user navigating a path while attempting to avoid obstacles in the path, such as the icebergs shown on the lower left portion of the screen. This is the visuomotor "Navigation" task for the Project: EVO cognitive assessment. The data from this task is also collected and analyzed. Screen shot 303 shows the user multi-tasking: responding to a target while also navigating down a path.

Figure 4:
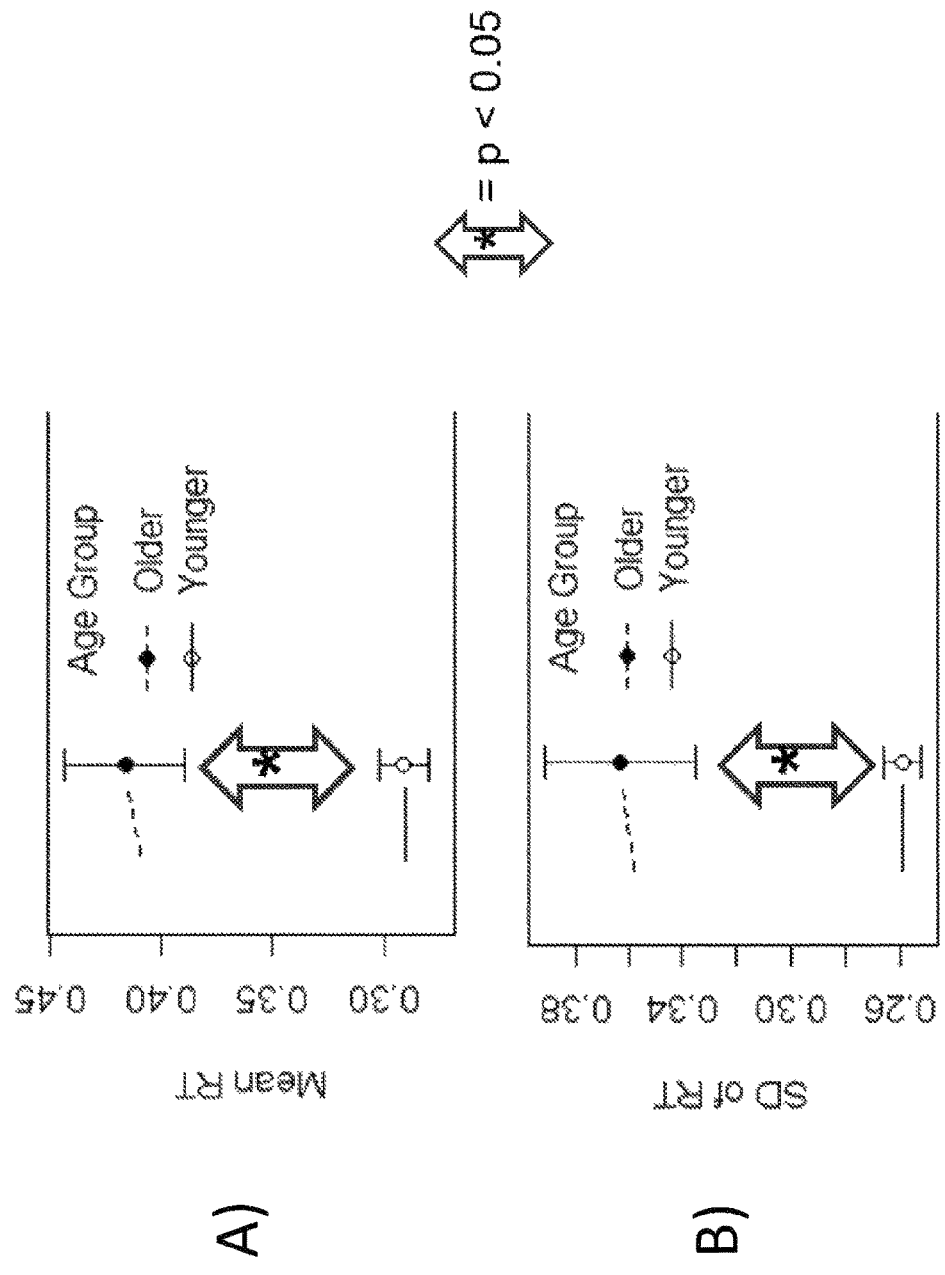
FIG. 4 depicts results of a pilot study of the exemplary preferred embodiment of the cognitive assessment tool.

FIG. 4 contains the results of a pilot study of Project: EVO assessment. This study compared the performance of young adults to older adults while multi-tasking. Both the mean of the reaction time (A) and the standard deviation of reaction time (B) were significantly different between the younger adults and older adults. These performance measures were taken while the participants were engaged on a multitask that included (1) a perceptual reaction task in which the user was made to perform a two-feature reaction task including target stimuli and distractor stimuli by tapping on the screen or refraining from tapping, respectively, and (2) a visuomotor tracking task using the iPad accelerometer to steer an avatar through obstacles down a graphical course.

Details of various aspects of the cognitive assessment tool are described below.

Multi-Tasking

Multi-tasking refers to a situation where a person is performing two or more tasks simultaneously. It also denotes a situation where a person is rapidly switching to and from different tasks or is performing multiple, different, short tasks in a row. Multi-tasking is a unique process because it requires the executive function controls that 1) decide to perform one action instead of another and 2) activate the rules of the current task. Because multi-tasking has become increasingly a common occurrence, researchers have attempted to understand the mental processes underlying multi-tasking and the relationship between multi-tasking and academic achievement, learning, and memory (Charron and Koechlin, "Divided Representation of Concurrent Goals in the Human Frontal Lobes" Science, 328: 360-363; Mayer and Moreno, 2003 "Nine ways to reduce cognitive load in multimedia learning" Educational Psychologist, 38(2): 43-52; Junco and Cotton, 2010 "Perceived academic effects of instant messaging use" Computers & Education, 56(2):

370-378). In these settings, the main feature being investigated is the decay in performance in the multi-task scenario relative to the scenario where individuals are only performing one single-task component of the multi-tasks.

Additionally, recent purpose-built cognitive paradigms have been constructed to study this phenomenon by measuring the difference between single-task performance and performance in the same task while multi-tasking. The resulting multi-tasking cost is used for cognitive diagnostic (Int. Pat. No. WO2012/064999A1 by Gazzaley, A.).

Uniquely, our research finds that, contrary to what was previously assumed, performance data collected in the multi-tasking environment, other than the previously useful multi-tasking cost data, is also informative of a user's cognitive state, and in some cases can be a more informative method than traditional cognitive assessments and traditional multi-tasking "cost" measurements.

Computer Device

Performance of the many tasks that are accomplished on a computer can be measured with incredible accuracy, often surpassing the ability of the human to measure, store, and analyze the inputs of a user. The cognitive assessment tool described herein may be implemented on a computer processing system with an input component. The computer processing system is suitable because it allows for the presentation of two tasks and measurement of user responses to the two tasks at the same time, something humans are not capable of doing with fidelity and reliability. The computer processing system also allows for the adaption of difficulty of both tasks independently. Additionally, without the temporal resolution that the computer processing system is able to provide, the performance measurements would not be effective cognitive measures. For example, the computer device can measure differences in the inputs, such as the millisecond timing of keystrokes on a keyboard or clicks on touch screen, that are imperceptible to a human trying to measure the same task. In one embodiment of our disclosed methods, the difference in mean reaction time to a perceptual reaction task between young adults and old adults is around one tenth of a second.

Computer devices have become integrated into many people's daily lives. They are now used for many types of communication, processing of data, and for entertainment purposes such as electronic video games. Whereas this is not crucial for other cognitive tests, the ubiquitous presence of computer devices and multi-tasking allow for passive measurements of everyday computer use as part of a cognitive assessment.

In one embodiment, the present disclosure provides computer-implemented methods for measuring cognitive function of an individual, wherein the method is implemented using a computer device having an input component. In some embodiments, the computer device is selected from the group consisting of a desktop computer, a laptop computer, a computer tablet device, a smart phone device, and a video game device. In some embodiments, the computer input device is selected from the group consisting of a mouse component, a stylus computer, a keyboard component, a microphone, a sensor of physical state of the user (e.g., accelerometer and/or gyroscope), and a touch screen display. It is appreciated that many such computer input methods are available, and advances in computing technology will continue to provide new types of inputs. The method of the current patent is dependent on an input modality, but importantly is independent of a specific type of input modality so long as the ability to reliably measure the input is maintained, and thus the disclosed methods are applicable to current and future input modes.

Tasks

In one embodiment, a task includes stimuli presented on a computer device, evoking responses from the user. The stimuli that evoke responses from the user may come in multiple forms. The stimuli may be chosen from a variety of stimulus modalities known in the cognitive art, including but not limited to visual, auditory, tactile, language based or symbolic. The user response may also come in many different forms. The user response can also be chosen from a variety of modalities known in the art, including but not limited to binary input (yes/no or true/false), choosing one or more options among many, constant input (continuously adjusting to changing stimuli e.g. steering a car down a road), language based (typing or speaking a response), elements of biofeedback measured by a sensor connected to the computer-device (EEG signals, accelerometer readings, etc.), and the like.

In one embodiment, a user is considered engaged in multi-tasking if they are attending to and performing at least two tasks simultaneously under a few conditions. First, for example, the tasks may be considered to be simultaneous if the user is providing inputs to the two tasks as the same time. For instance, a user could be providing movement inputs for a motor task through a joystick and at the same time providing inputs to a reaction task with a mouse. Second, for example, the tasks may be considered to be simultaneous if the user switches between the two tasks within a set amount of time. The set amount of time for switching could be considered about 1 tenth of a second, 1 second, about 5 seconds, about 10 seconds, about 30 seconds, about 1 minute, or 2 or more minutes. The tasks can be presented to the user in any order known to work by one skilled in the art. For example, tasks may be presented in a rotating order (e.g., A, B, C, . . . n, A, B, C . . . n, etc.); in a predetermined order set by someone familiar for a particular purpose (e.g. A, B, A, B, C, A, B, C, D, etc. or A, A, A, B, B, C); in a random order; or in a random order with some conditions on the distribution of certain tasks. For instance, a user could be providing language based inputs to an email task for 1 minutes and responding to instant messages with language based inputs for 30 seconds before returning to the email task for 2 minutes. Third, for example, the tasks may be considered to be simultaneous if the tasks are completed within a short time period and are done right after one another with no break. Short time period is considered about 1 tenth of a second, about 1 second, about 5 seconds, about 10 seconds, about 30 seconds, about 1 minute, or 1-2 minutes. For instance, a user may engage in web browsing for 30 seconds, followed by instant messaging for 30 seconds, followed by game play for 30 seconds. Fourth, for example, the tasks may also be considered simultaneous if the user is instructed to complete at least two tasks within a set period of time. For two tasks, that period of time could be about 10 seconds, about 30 seconds, about 1 minute, about 4 minutes, about 5 minutes, about 7 minutes, or 10 minutes or more.

The tasks in which the user is engaged may have levels of difficulty. In some embodiments, at least one task may have a constant level of difficulty. In some embodiments, at least one task has a variable level of difficulty. When difficulty can be varied for a task, it can be varied based on a schedule that does not depend on user inputs or it can be varied based on the inputs of the user which is referred to herein as an "adaptive task." In one embodiment, the adaptive task increases in difficulty when the user gives a correct response and decreases in difficulty when a user gives an incorrect response. Though the method of increasing a difficulty of a task is dependent on the specific task, generally the difficulty of a task may be increased by increasing the number of features a user must attend to, decreasing the perceptual salience, increasing the frequency of required responses from a user, among other ways known to one skilled in the art.

For the purposes of this description, tasks performed on a computer device may be divided into two categories. The first category of tasks are those in which a user is asked to respond a certain way to a specific stimuli for the purposes of cognitive assessment, and/or the tasks are purposefully structured to serve as an assessment (hereinafter referred to as "active tasks"). The second category of tasks are those in which a user is voluntarily responding to stimuli for purposes other than cognitive measurement, and/or are not structured to be a reliable measurement modality (hereinafter referred to as "passive tasks"). The term "task" in this disclosure encompasses both active and passive tasks unless otherwise specified.

There are numerous passive tasks that can be monitored by the computer device without being obtrusive to the user. Suitable passive tasks include but are not limited to responding to written communication through a keyboard, web browsing with mouse clicks, web browsing through the keyboard, reading and progressing to new content through mouse clicks or touch screen taps, playing games with inputs described above, editing photos, and any other tasks that involve using one's smartphone or tablet or other mobile device and have tactile, auditory, or motion input, and other tasks in the same vein. The length of the passive task can be considered the entire time a user is engaged in the task at one time or a pre-determined amount of time ranging from 30 seconds or less, about 1 minute, about 4 minutes, about 7 minutes, about 10 minutes, to 15 minutes or more.

In some embodiments, the user performing at least two tasks simultaneously involves the user performing at least one passive task. In some embodiments, the user performing at least two tasks simultaneously involves the user performing at least two passive tasks simultaneously. One embodiment of a user performing at least two passive tasks simultaneously is a user writing an email and also responding to instant messaging questions from a co-worker. Another preferred embodiment of a user performing two passive tasks simultaneously is a user reading a web page and also monitoring a twitter feed.

In a preferred embodiment of the disclosed methods, a user performing at least two passive tasks simultaneously involves a user performing at least two passive tasks simultaneously in a video game. Computerized video games often present situations in which a user must perform more than one task. For example, a user can be walking an avatar around a game environment while simultaneously changing weapons. It has already been shown that casual video games overall performance correlates to specific cognitive functions (Baniqued, Lee, Voss, et al., "Selling points: What cognitive abilities are tapped by casual video games?" Acta Psychol (Amst.) 2013; 142(1):74-), but the cognitive assessment tool described herein improve upon that state of the art because it is based on situations in which a user is multi-tasking in the gaming environment and it takes specific user inputs from game play as performance measures instead of just overall score on the game.

There are also many ways to provide active tasks for a user. For example, there are multiple tasks that evaluate a user's cognitive abilities in the following domains: attention, memory, motor, reaction, executive function, decision-making, problem-solving, language processing, and comprehension, among others. The active task can last as long as the user is willing to engage in the task or for a prescribed amount of time, 30 seconds or less, about 1 minutes, about 4 minutes, about 7 minutes, about 10 minutes, and 15 minutes or more.

In some embodiments, a user performing at least two tasks simultaneously involves a user performing at least one active task. In some embodiments, a user performing at least two tasks simultaneously involves a user performing at least two active tasks simultaneously. The two tasks performed simultaneously can be assessing the same cognitive domain listed above or assessing different cognitive domains. A preferred embodiment of a user performing at least two active tasks simultaneously is a user performing a visuomotor task and a perceptual reaction task simultaneously. In one embodiment, performing a visuomotor task involves a presentation of visual stimuli that require fine motor movement as reaction to the stimuli. In some embodiments, the visuomotor task is a continuous visuomotor task, altering the visual stimuli and recording the motor movements of the user at, e.g., 1, 5, 10, or 30 times per second. One embodiment of stimuli for a visuomotor task requiring fine motor movement may be a visual presentation of a path that an avatar must stay on. This path may have obstacles that the user is instructed to avoid and/or specific locations that the user in instructed to cross. In such an embodiment the fine motor reaction could be, among other things, tilting a device with an accelerometer to steer the avatar to keep it on the path, while avoiding the obstacles, and crossing the desired locations. In one embodiment, presenting a perceptual reaction task involves presenting both distractor stimuli that do not require a response from the user and target stimuli that require a response from a user. In one embodiment, the distractor stimuli and the target stimuli are differentiated by shape. In another embodiment, the distractor stimuli and the target stimuli are differentiated by color. In another embodiment, the distractor stimuli and the target stimuli are differentiated by shape and color, for example a user has to respond to red circles but not green circles or red squares. In some embodiments, a user performing at least two tasks simultaneously involves a user performing at least three active tasks simultaneously. A preferred embodiment of a user performing at least three active tasks simultaneously is a user performing a visuomotor task, a perceptual reaction task, and a memory tasks simultaneously.

In some embodiments, the tasks the user is performing are adaptive tasks. The tasks can be adapted or modified in difficulty by any methods known by one of ordinary skill in the art, such as staircase procedures and maximum likelihood procedures. Such difficulty adaption may be used to determine the ability of the participant. In a preferred embodiment, the difficulty of the task adapts with every stimuli that is presented, which could occur more often than once every 10 seconds. In an alternative embodiment, the difficulty of a continuous task adapts on a set schedule, such as, e.g., every 30 seconds, 10 seconds, 1 second, 2 times per second, or 30 times per second.

In some embodiments, a video game is used to provide an assessment medium in which a user is asked to perform at least two active tasks simultaneously. One advantage of presenting these specific tasks in a video game is that it allows features that can encourage the participant to perform at the highest levels possible, such as by providing rewards and creating an engaging interface. In a preferred embodiment, a user performing at least two active tasks simultaneously in a video game involves a user performing a visuomotor task and a perceptual reaction task simultaneously. In one embodiment, presenting a perceptual reaction task involves presenting both distractor stimuli that do not require a response from the user and target stimuli that require a response from a user. In one embodiment, the distractor stimuli and the target stimuli are differentiated by shape. In another embodiment, the distractor stimuli and the target stimuli are differentiated by color. In another embodiment, the distractor stimuli and the target stimuli are differentiated by shape and color, for example a user has to respond to red circles but not green circles or red squares.

User Inputs

The user may respond to tasks by interacting with the computer device. In one embodiment, the cognitive assessment tool obtains user response through an input modality, but importantly the specific type of input modality can vary so long as the ability to reliably measure the input is maintained, and thus the described methods are applicable to current and future input modes. Examples of inputs for a desktop computer include a keyboard for alpha-numeric or directional inputs; a mouse for go/no go clicking, screen location inputs, and movement inputs; a joystick for movement inputs, screen location inputs, and clicking inputs; a microphone for audio inputs; and a camera for still or motion optical inputs; sensors such as accelerometer and gyroscopes for device movement inputs; among others. Example inputs for a video game system include but are not limited to a video game controller for navigation and clicking inputs, a video game controller with accelerometer and gyroscope inputs, and a camera for motion optical inputs. Example inputs for a mobile device or tablet include a touch screen for screen location information inputs, virtual keyboard alpha-numeric inputs, go/no go tapping inputs, and touch screen movement inputs; accelerometer and gyroscope motion inputs; a microphone for audio inputs; and a camera for still or motion optical inputs, among others. Additionally, these devices can integrate physiological sensors to incorporate inputs from the user's physical state. The method of integrating physiological sensors as inputs is dependent on having a physiological input, but importantly is independent of the specific type of input modality, and thus the described methods are applicable to current and future physiological input mode. Examples of physiological measurements for the disclosed methods include but are not limited to electroencephalogram (EEG), magnetoencephalography (MEG), heart rate, heart rate variability, blood pressure, weight, eye movements, pupil dilation, electrodermal responses such as the galvanic skin response, blood glucose level, respiratory rate, and blood oxygenation.

Measurements

It is known to one skilled in the art that multi-tasking tests are useful in that they allow one to measure the difference in performance of a task when multi-tasking and when single-tasking (multi-tasking cost) as a cognitive measure (Int. Pat. No. WO2012/064999A1 by Gazzaley, A.). However, the inventors have unexpectedly found that other measures of performance during multi-tasking are as useful as, or in some cases more useful than, multi-tasking cost. The multi-tasking performance measures may be considered to be fundamentally different measures of cognitive function than multi-task cost measures and traditional single-task cognitive measures known to one skilled in the art. The following measures described are all ones taken while a user is in a multi-task environment, unless it is explicitly mentioned that it is not measured while multi-tasking. It is appreciated that any of a variety of cognitive performance measurements usually used for single-task may be useful in the disclosed methods. Suitable measurements can be made on both adaptive and non-adaptive tasks, as described in the task section above, as the case may be.

Performance measures may be dependent on the specific task presented and the category of cognitive function that is being examined. As previously stated, one embodiment can have tasks associated with one or more of the following cognitive domains: attention, memory, motor, reaction, executive function, decision-making, problem-solving, language processing, and comprehension, among others. In these domains, performance measures of user inputs or responses may be used to create the measure indicative of cognitive function. For example, performance measures may include response time, task completion time, number of tasks completed in a set amount of time, preparation time for task, accuracy of responses, accuracy of responses under set conditions (e.g., stimulus difficulty or magnitude level and association of multiple stimuli), number of responses a participant can register in a set time limit, number of responses a participant can make with no time limit, number of attempts at a task needed to complete a task, movement stability, accelerometer and gyroscope data, self-rating, among others known in the art.

In one embodiment, the performance measure may be reaction time. In a preferred embodiment, reaction time is measured as the reaction time to a perceptual reaction task. Further, if the perceptual reaction tasks includes stimuli that are distractors, those that the participant should not respond to, the reaction time can be measured as either the reaction time to any response to any stimuli, reaction time only to responses to the correct non-distractor stimuli (target stimuli), or reaction time to distractor stimuli—also known to one skilled in the art as the "false alarm" reaction time.

In some embodiments, the performance measure may be correctness of responses, such as the quantity of correct responses over a set number of stimuli. In a preferred embodiment, the correct responses may be measured as the correct responses to a perception reaction task. For a perception reaction task with distracters (i.e., stimuli the user should not respond to), correct reactions may be calculated as the number of times a user responds to the target stimuli, or as the number of responses to the target stimuli added to the number of non-responses to the distractor stimuli. In some embodiments, the performance measure may be the quantity of incorrect responses to a task over a set number of stimuli. In a preferred embodiment, the incorrect responses may be measured as the incorrect responses to a perception reaction task. For a perception reaction task with distracters (i.e., stimuli the user should not respond to), incorrect reactions may be calculated as the number of times a user responds to the distractor stimuli, or as the number of responses to the distractor stimuli added to the number of non-responses to the target stimuli.

In some embodiments, the performance measure may be the stimuli magnitude at which the user is able perform a task correctly or incorrectly in an adaptive task. In a preferred embodiment, the stimuli magnitude may be the speed down a path for a visuomotor "navigating" task. In another preferred embodiment, the stimuli magnitude may be the reaction window time given to respond to a perceptual reaction task.

From the performance measures calculated from user inputs, further analysis can be completed to create more complex measures of cognitive function. In some embodiments the measure indicative of cognitive function reported is a complex cognitive measure. There are several methods of creating complex cognitive measures, e.g.: using standard statistical summary methods, applying signal detection theory, applying psychophysics performance metrics, combining data to create a composite measures, and examining measures over time.

In some embodiments the complex cognitive measure may be a statistical summary measure. Summary statistics employed by one skilled in the art include: mean, variance through standard deviation or standard error, running average, time spent in a certain performance level, being above or below a specified value, percent, correlation, Root Mean Square Error (RMSE), R2 correlation coefficient, confidence intervals, fit to standard statistical distributions such as T-score or Z-score, summary according to a normative data set, Bayesian statistical methods, measurements created from a Principle Component Analysis, measurements created from machine learning, specifically pattern recognition between groups, and parameters from applying statistical model such as regression coefficients and Monte Carlo simulation parameters, and the like.

In one embodiment, the statistical summary measurement recorded may be the mean performance at a task over a period of time. In a preferred embodiment, the mean performance at a task consists of the mean performance when the task continuously adapts difficulty to the user's previous performance on the task. A period of time can be chosen as the amount of time a person performs a task at one time or can be a predetermined amount of time such as about 30 seconds, about 1 minute, about 4 minutes, about 10 minutes, or more than 10 minutes. In a preferred embodiment, the mean performance game-level is measured as the mean reaction time window for a perceptual reaction task when that window is increased when the user responds incorrectly and decreases when a user responds correctly. Further, reaction time windows can be labeled as "levels" in a game, with the level number increasing as the reaction time window decreases. In some embodiments, the mean performance at a task can be measured as the mean performance game-level. In some embodiments, the mean performance game-level is the mean performance game-level of a perceptual reaction task. In another preferred embodiment, the mean performance level is the mean stimuli magnitude of an adaptive visuomotor task. Further, for a "navigating" visuomotor task, navigation speed and number of obstacles can be used to determine a navigation game level, with the level increasing with increase speed and/or increasing number or size of obstacles. This navigation game level can be used to calculate the mean performance level.

In another embodiment, the statistical summary measurement may be the standard deviation of performance level at a task over a period of time. In a preferred embodiment, the standard deviation of performance level at a task is the standard deviation of performance level when the task continuously adapts difficulty to the user's previous performance on the task. A period of time can be chosen as the amount of time a person performs a task at one time or can be a predetermined amount of time such as about 30 seconds, about 1 minute, about 4 minutes, about 7 minutes, about 10 minutes, or more than 10 minutes. In a preferred embodiment, the standard deviation of performance level is measured as the standard deviation of the reaction time window for a perceptual reaction task when that window is increased when the user responds incorrectly and decreases when a user responds correctly. Further, reaction time windows can be labeled as "levels" in a game, with the level number increasing as the reaction time window decreases. This game-level can be used to calculate the task's standard deviation of performance level in addition to the actual reaction time window. In another preferred embodiment, the standard deviation of performance level is the mean stimuli magnitude of a visuomotor task. Further, for a "navigating" visuomotor task, navigation speed, shape of the course, and number of obstacles can be used to determine a navigation game level, with the level increasing with increase speed, increasing frequency of turns, decreasing turning radius, and/or increasing number or size of obstacles. This navigation game-level can be used to calculate the standard deviation of performance level.

In one embodiment, the statistical summary measurement may be mean reaction time over a period of time. A period of time can be chosen as the amount of time a person performs a task at one time or can be a predetermined amount of time such as about 30 seconds, about 1 minute, about 4 minutes, about 7 minutes, about 10 minutes, or more than 10 minutes. In a preferred embodiment, mean reaction time is measured as the mean reaction time to a perceptual reaction task. Further, if the perceptual reaction tasks includes stimuli that are distractors, those that the participant should not respond too, the mean reaction time can be measured as either the mean reaction time to any response to any stimuli, mean reaction time only to responses to the target stimuli, or mean reaction time to distractor stimuli—also known to one skilled in the art as the "false alarm" reaction time.

In one embodiment, the statistical summary measurement taken may be the standard deviation of a set of reaction times. These reaction times can be compiled for analysis by choosing all reaction time events while a person performs the task analyzed or in a set amount of time such as about 30 seconds, about 1 minute, about 4 minutes, about 7 minutes, about 10 minutes, or more than 10 minutes. In a preferred embodiment, standard deviation of reaction time is measured as the standard deviation of reaction time in a perceptual reaction task. Further, if the perceptual reaction tasks includes stimuli that are interference/target stimuli and distractor stimuli the standard deviation of reaction time can be measured as either the standard deviation of reaction times to any response to any stimuli, reaction times only to responses to the target stimuli, or reaction times to distractor stimuli.

In one embodiment, the statistical summary measurement taken may be the correlation of performance level with the order in which a task is performed. In one preferred embodiment, correlation of performance level with the order in which a task is performed is the correlation of game-level of a perceptual reaction tasks with the order of the perceptual reaction task. In one preferred embodiment, correlation of performance level with the order in which a task is performed is the correlation of navigation game-level of a visuomotor tasks with the time engaged in the visuomotor task. In one preferred embodiment, correlation of performance level with the order in which a task is performed is the correlation of hit rate and false alarm rate (as described below under signal detection theory) with the order of the perceptual reaction task.

In some embodiments, the statistical summary measurement taken may be created from Bayesian statistical methods. For example, the Bayesian analysis can include but is not limited to the probability of a correct response given an incorrect response and the probability of an incorrect response given a correct response.

In some embodiments, the statistical summary measurement taken may be created via Principal Component Analysis or a similar technique to transform multiple direct performance measures into a smaller set of indirect measures summarizing the most significant contributors to variability within the measurements. With a Principal Component Analysis method, the multi-tasking performance measures from multiple samples are combined into one data set. For example, the set may consist of performance measures A, B, C, D, and E for a set of experiment participants (Participants #1-100). This data set may be the input to an orthogonal transformation that converts the performance measures A-E into a set of linearly uncorrelated variables, named the principle components. The outputs may be composed of eigenvectors of the original variable set. When using such a method, the outputs or the principle components are themselves a metric of cognitive function. The Principle Component Analysis is one way of creating composite variables.

In some embodiments, the statistical summary measurement taken may be derived from machine learning. In one embodiment, classification techniques may be used to train a computer data model using the performance measures of a labeled population of subjects (e.g., subjects with known cognitive disorders or abilities). The trained computer data model may be applied to a user's performance measures to predict which population label (e.g., cognitive disorder) should be assigned to the user. For example, machine learning may be implemented by using cluster analysis. Each observation of participating individuals (e.g., the cognitive assessment tool may be used to determine performance measures of each individual) is categorized into subsets or clusters. In one case, the subset or cluster labels may be the cognitive disorders each participant in an experiment is diagnosed with. Using the cluster analysis machine learning techniques, outputs may represent similarity metric of each subset and the separation between different subsets. In a different example, a supervised machine learning may be based on artificial neural networks. In such a case, the performance measures of participating individuals with known cognitive abilities may be used to train the neural network algorithm to better understand the complex relationships between the different performance measures. Once trained, the neural network may be applied to a user's performance measures to output a cognitive measure, which may represent a prediction of his/her cognitive abilities.

In another embodiment, regression or Monte Carlo techniques may be used to generate computer data models to describe observed performance measures and predict certain user's cognitive abilities based on his/her cognitive performance. In some embodiments, the ability being predicted may be outside of the assessment environment (e.g., gaming environment), such as external tests of attention or performance on standardized academic tests. For example, a model may be trained using the multi-task performance measures of a group of individuals and their external measures of cognition (e.g., their known cognitive abilities, including cognitive disorders, attention span, performance on standardized tests, etc.). Using Monte Carlo or regression techniques, a computer data model may be trained to predict the external measure of cognition of an individual using that individual's multi-task performance measures. In addition to the multi-task performance measures, other potentially predictive variables may also be used, such as EEG and demographic measures.

In one embodiment, the statistical summary measurement taken may be based on a summary of accelerometer data. Statistical summaries of the accelerometer vector components (x, y, z), taken individually or as a composite, may be used to measure performance. Statistical summaries can be but are not limited to, e.g., the mean and standard deviation. In addition, accelerometer data can be compared to an ideal function from which deviance from the ideal measures can be computed. In addition, accelerometer data can be treated as a waveform to measure the spectral properties of the user's performance. An example of such an analysis may involve a Fourier transform of the accelerometer data to produce gain, phase, and amplitude values representing the user's performance profile over the course of gameplay. In one embodiment, the accelerometer data may be captured at, e.g., 30 times per second, so that the user's exact movements of the mobile device are recorded. The raw accelerometer data would indicate the amount of acceleration in the x, y, and z directions at any moment in time. The accelerometer data, which has the form of a finite sequence of equally spaced samples can be put through a Fourier transform, which outputs the information about the frequency domain, or a list of coefficients of a finite combination of sinusoids, ordered by their frequencies. The outputs may indicate the user's motor response capabilities, the degree of cognitive and motor demand placed on them by the visuomotor task, and the timing of these demands with respect to contemporaneous perceptual reaction task trials.

In some embodiments the complex cognitive measure may be computed using signal detection theory. Signal detection theory can be used by one of ordinary skill in the art to calculate a sensitivity index (d' or A'), Bias, ROC, hit rate, false alarm rate, and the like from the user responses and performance measures.

In a preferred embodiment, the metric from signal detection theory representing cognitive function may be the hit rate from a perceptual reaction task. In that context, hit rate may be defined as the number of correct responses to a target stimuli divided by the total number of target stimuli presented. In another preferred embodiment, the metric from signal detection theory representing cognitive function may be the false alarm rate from a perceptual reaction task. In such context, the false alarm rate may be defined as the number of responses to a distractor stimuli divided by the number of distractor stimuli presented. In another preferred embodiment, the metric from signal detection theory representing cognitive function may be the miss rate for a perceptual reaction task. In such context, the miss rate may be the number of non-responses to a target stimuli divided by the number of incorrect responses, including the non-responses to a target stimuli added to the number of responses to a distractor stimuli. In another preferred embodiment, the metric from signal detection theory representing cognitive function may be the correct response rate, defined as the proportion of correct responses not containing signal. The correct response rate may be calculated as the number of non-responses to the distractor stimuli divided by the number of non-responses the distractor stimuli plus the number of responses to the target stimuli.

In some embodiments the complex cognitive measures may be created from psychophysics methods of the user responses or performance measures. Psychophysics theory can be used by someone skilled in the art to measure a user's thresholds through the method of limits, method of constant stimuli, or method of adjustment, among many other measurements.

In one embodiment, the psychophysics metric determined from user inputs may be based on performance threshold. This threshold may be defined as the maximum stimulus magnitude (such as speed in a visuomotor navigation task) of a task for which a user can achieve a specified ratio of correct responses to incorrect responses in an adaptive task over time. For instance, the threshold may be defined as the maximum stimulus magnitude of a task for which a user can correctly perform the task about 1%, about 10%, about 50% of the time, about 70% of the time, about 80% of the time, or between 90-100% of the time. The threshold may also be defined as the maximum stimulus magnitude of a task for which a user achieves a specified ratio of correct responses to incorrect responses when the stimulus magnitude is increased incrementally. In addition, the threshold may be characterized by the quantity or percent of stimuli that are responded to correctly above or below the threshold level in an adaptive task. In a preferred embodiment, the performance threshold may the reaction time window at which the user can to continuously achieve 80% correct responses to a perceptual reaction task. Further, reaction time windows may be labeled as "levels" in a game, with the level number increasing as the reaction time window decreases. This game-level may be used to represent the task's performance threshold in addition to the actual reaction time window. In another preferred embodiment, the performance threshold may be the stimulus magnitude (i.e., speed of the object of the task) at which a user is able to perform a visuomotor task at 80% correct. Further, for a "navigating" visuomotor task, navigation speed and number of obstacles can be used to determine a navigation game-level, with the level increasing with increase speed and/or increasing number or size of obstacles. This navigation game-level may be used to represent the navigation performance threshold. In another preferred embodiment, the performance threshold may be the combination of the maximum stimuli magnitudes at which the user performs a visuomotor task at 80% correctness and perceptual reaction task at 80% correctness. For instance, this measurement may be represented as the mean of the game-levels previously described in this paragraph. In another preferred embodiment, the performance threshold may be the reaction time threshold.

In some embodiments the complex cognitive measure may be a composite measure. Examples of composite measures are combinations of two or more performance measures from one task, combinations of two or more performance measures from more than one task, and combinations of performance measures with external information.

In some embodiments, the composite measure may be a composite of at least two measures from the same task. Composite measures may be created in at least two ways. In the first way, the composite measure may be one that is created prospectively to represent a known cognitive or psychological construct. A list of such constructs follow. In a preferred embodiment, the composite of two measures from the same task is the reaction time for a response to a stimuli divided by the reaction time window in which a user can possibly respond to the reaction time in the perceptual reaction task, which provides an indicator of how the user allocated the time allotted to them to respond. In another preferred embodiment, the composite of two measures from the same task is the mean reaction time to stimuli divided by the standard deviation of the reaction time in a perceptual reaction task, which provides a normalized measure of reaction time variability that can be used to compare across subjects with diverse baseline characteristics. In another preferred embodiment, the composite measure includes the mean reaction time added to or averaged with the standard deviation of reaction time for all responses, which provides a way of balancing the impact of baseline performance and variability. In another preferred embodiment, the composite of two measures from the same task is the correlation of the reaction time to stimuli magnitude or difficulty of the task. The correlation of the reaction time to the stimuli magnitude of a task can be the correlation of the reaction time to and the game-level of a perceptual reaction task when the game-level changes during measurement. This is another indicator of how the user allocates the time allotted to them.

In some embodiments, the composite measures may be a composite of at least two measures from at least two different tasks. In one embodiment, the composite measure of two measures from two different tasks may be the difference in performance of the two tasks. In a preferred embodiment, the difference in performance may be the difference in the game-level of a perceptual reaction task and the game-level of a navigation task. The statistical summary measurement of the measure may be whether or not the difference in the performance game-level of the navigation task and the performance game-level of the perceptual reaction task is greater than or less than the running average of the difference. This measurement speaks to the degree to which the user is adjusting their strategy over time to allocate their resources between the two tasks. In one embodiment, the composite measure of two measures from at least two different tasks may be tradeoff summary. One way to calculate the tradeoff summary may be by dividing the threshold for one task by the threshold for another task. In a preferred embodiment, the tradeoff summary may be the game-level threshold for a perceptual reaction task divided by the game-level threshold for a visuomotor task. The tradeoff summary is another indicator of the user's allocation of resource between tasks.

In some embodiments, the composite measure may be a composite of multi-task performance measures and external information. External information, or information not obtained from the instant multi-tasking assessment, that can be useful for determining cognitive measures include measurements from the same task under different circumstances, measurements from of a different cognitive task, performance on non-computerized tasks, non-performance information such as demographic information about the user, symptom and disease information, geographic and other contextual information, and the like. In one embodiment, the composite of user inputs and external data may be the composite of multi-tasking performance measures and different performance measures of user inputs while single-tasking. This composite variable is distinguished from the prior interference or multi-task cost measurements because these measures do not directly compare the same performance variable in the single-task and multi-task environment. This type is often a representation of the second way of creating composite cognitive measures, by using statistical methods or models to create unique variables not prospectively determined to evaluate a specific construct, though a construct may be determined afterwards. Examples of methods for creating such variables are Principal Component Analysis and neural networks machine learning. In a preferred embodiment, the composite of single-task and multi-task measurements may be the aggregate of 1) standard deviation of a perceptual reaction task game-level at which a the user correctly reacts to a non-distractor stimuli within the time window while single tasking, and 2) mean reaction time of the correct response to non-distractor stimuli while multi-tasking. In another preferred embodiment, the composite of single-task and multi-task measures may be the quantity (standard deviation of a game-level of a perceptual reaction task performed in isolation plus the mean reaction time of a perceptual reaction task while multi-tasking minus the mean reaction time of a perceptual reaction task in isolation) divided by two.

In some embodiments, patterns of performance measures created from the multi-tasking assessment tool may be used for evaluation of cognitive abilities. For example, pattern recognition may be based on performance measures of a set of neurotypical individuals and distinct groups with different known medical diagnoses. These groups may be symptomatically similar, such as having sensory processing disorder and autism, or having cerebrovascular dementia and Alzheimer's disease. By using, e.g., machine learning or classification analysis to process the different types of performance measures from the multi-tasking assessment tool and known cognitive assessments, clinically similar groups may be able to be diagnosed or differentiated. For example, if a set of three predictive measures are used, such as reaction time variability, game level of a continuous motor task, and false alarm rate of a reaction task, the Alzheimer's group may be differentiated by high false alarm rates and the cerebrovascular group may be differentiated by both the lower game level of a continuous motor task and the high false alarm rate.

In some embodiments, the complex cognitive measure may be a measure taken over time. Measures taken over time include change in user inputs over time, progression in a task or game, and interaction variables with a task or game.

In one embodiment, the measure taken over time may be the change in user inputs over time. As is known in the art, the ability for one to acquire or maintain particular skills can change with cognitive function. In one preferred embodiment this change in user inputs over time may be calculated as the change in any metric over a specific period of use, representing a change in the task performance. The specific period of use in these cases may be time based such as 10 minutes of task engagement, 20 minutes task engagement, 30 minutes task engagement, or 60 minutes of task engagement. In other cases, the specific period of use may be determined by the number of instances the task was engaged in by the user, such as the number of times a game was played (2 times, 4 times, 7 times, 10 times, 25 times, 35 times, 50 times, 70 times, 100 times, 140 times, or 150 more times) or the number of written communications created. The specific period of use may also be determined by a set time period that does not account for the number of instances or amount of time a task is completed. For example, the change in user inputs can be calculated as the change over 1 hour, 1 day, 2 days, 1 week, 2 weeks, 1 month, 3 months, 6 months, 1 year, or more than 1 year. The reverse of this metric may also be useful, namely the amount of time or engagement it takes to achieve a specific change in a measure.

In one embodiment, the change in a user input over time may be the change in mean reaction time from the first time a user engaged in a perceptual reaction task to the seventh time a user engaged in the same task while multi-tasking. In another preferred embodiment, the change in skill level may be measured as the length of time required to attain a specified change in user inputs. For example, the change in user inputs may be measured as the time it takes to reduce the mean reaction time by 100 milliseconds in a perceptual reaction task or the time to achieve the next game level of threshold performance.

In one embodiment, at least two tasks may be performed by the user in a video game environment and the complex cognitive measure of user inputs over time may be the ability of the user to progress through the game. One preferred embodiment of user progress through the game is the measurement of the amount of time a user spends at levels close to or exceeding the users previously calculated threshold performance level of both tasks. This amount of time can be reported in summary methods known to one skilled in the art such as the maximum time spent at the specific levels and the total time spent over many measurements, among others. Another preferred embodiment of user progress through the game may be the number of levels a user can achieve in a set period of time. Another preferred embodiment of user progress through the game may be the number of times a user fails to meet or improve the threshold levels of performance to move on to the next game level.

In another embodiment, the inputs from the user may be used to create complex cognitive measures over time that represent measures of behavior and interaction with the cognitive assessment tool. One preferred embodiment of measuring interaction with the cognitive assessment tool is the measurement of compliance—whether the user interacts with a device in the way in which he or she is instructed. For instance, if a user is instructed to be in a multi-tasking environment for a set period of time or set number of task activities per day, the measure could be the percent of days in a month that user meets the requirements. Another preferred embodiment of the interaction measurement may be the measurement of the frequency of being in the multi-tasking environment. Another preferred embodiment of the interaction measurement may be the measurement of the patter of interaction with the device, for instance if the user engages is multi-tasking once per day or multiple times per day. In another embodiment, the complex cognitive measure that represents behavior may be the user's attention to irrelevant features of a video game. For example, if the stated goal of the game is to perform a visuomotor task and a perceptual reaction task in a video game, but a third task such a coin collection is also included, how often the user engages in the third task may be used to compute a cognitive measure.

As known by one skilled in the art, the measures described in this section may change when a user is giving maximum effort. Therefore, these measures may be taken over any time period or only when it can be identified that a user is giving maximum effort and each would have different cognitive meanings. In one embodiment, analysis of user inputs are isolated to the user inputs when the level of difficulty is near threshold levels for two or more adaptive tasks. In a preferred embodiment, the user inputs analyzed may be the user inputs for an adaptive visuomotor task and an adaptive perceptual reaction task when the game-levels of both tasks approach threshold levels.

It is appreciated that many of the passive tasks may not have standard cognitive measures that can be taken from the user input. In these cases there may be a few intermediate analysis steps on the user inputs. First is to identify when the multi-tasking is occurring and processing the data.

The identification of multi-tasking when passively monitoring a user can take a few different forms: determining when a user is switching frequently between different programs on a computational device and identifying when a user is engaged in a game that involves multi-tasking.

Processing the data from passive monitoring, as known to one skilled in the art, may involve identifying false multi-signaling flags, identifying and in some cases removing outlier data points, and tracking patients over a longer period of time to distinguish the signal from the noise. Following this set, the same techniques for evaluating user inputs in active tasks described herein may be applied.

Use of Measurements

The cognitive measurements described in this disclosure may be useful in many domains, including healthcare, employment evaluation, and education, among others.

In the medical setting, the cognitive assessment tool may be used by themselves, or with other clinical measurements, to diagnose a particular disease or medical condition. In another embodiment in the medical setting, the tool can be used to assess the severity of the cognitive deficit associated with a disease or medical condition. Particular populations for which such a cognitive measure would be beneficial for diagnosis are listed, in part, in the following section of the disclosure.

In one embodiment, the cognitive assessment tool may be used to monitor cognitive deficits. Monitoring cognitive deficits allows patients, clinicians, and care givers to track the progression of a disease. For example, in Alzheimer's disease some people have mild symptoms for many years, but others have symptoms that increase dramatically. If the cognitive symptoms can be measured it may give an indication when to take certain precautions such as not allowing the patient to live alone. Monitoring cognitive deficits also allows patients, clinicians, and care givers to monitor the response to any therapy or intervention, particularly in cases where the intervention is not known to be effective for an entire population. One example of such an embodiment is the use of the cognitive assessment tool to monitor the effectiveness of the administration of stimulant medications for a patient with attention deficit hyperactivity disorder (ADHD). Another use of the tool as a cognitive monitor is the observation of the presence and severity of any cognitive side effects from therapies with known cognitive impact, such as chemotherapy, or therapies with uncharacterized pharmacodynamics. In preferred embodiments, the monitoring may be repeated every 30 minutes, every few hours, every day, a few times a week, every week, every other week, every month, or every year.

In one embodiment, the cognitive assessment tool may be used to characterize the cognitive state of students. When used in schools and training programs, the described methods may be used to identify students who need special resources, identify students who need further neurological evaluation, identify students who would benefit from cognitive training, place students into the correct difficulty level of subject matter, and evaluate the effectiveness of educational curriculum and programs, among other things. The described methods may also be used to evaluate new curriculum or school programs, particularly those designed to improve cognitive abilities.

In one embodiment, the cognitive assessment tool may be used to assess cognitive abilities to evaluate the user's capabilities of functioning in a high demand job, particularly one that regularly relies on the user multi-tasking.

In some embodiments, the cognitive assessment tool may be used to measure effects of physical and emotional environments on cognitive function. The described methods may be used to test the effects of workplace environments on employees, surrounds of patients in hospitals and clinics, level of stress and its cognitive impact on any users, and much more.

In some embodiments, the cognitive assessment tool may be used to measure the effects of physical environmental exposures on cognitive function. In studies or for personal use, this tool may be used to understand the impact of chemicals, pollutants, food ingredients, and air quality, among others, on the cognitive function of the user.

In one embodiment, the cognitive assessment tool may be used to determine if a user has taken substances to alter his or her cognitive state. For example, this test may be used to screen parolees for drug use and identify those who should be considered for further testing.

Because this cognitive assessment tool may be deployed on multiple computer-device platforms, the described methods can be used anywhere there is a computer device. The described cognitive measurement tool has the advantage of being able to be useful in a doctor's office, in a hospital, in a school, in a workplace, in a home, in a moving vehicle, outside at a park, while walking down a street, and anywhere a mobile device can be carried.

As known to one skilled in the art, the user inputs can be measure one time, multiple times over a set time period or on a set schedule, or two times—specifically before and after a particular change is made, and the number of times a user's inputs are measured is determined by the function for which the cognitive measurement tool is employed.

Target Populations

Individuals that may benefit from the cognitive assessment tool may be any person. For any of the target populations described below, diagnostics, assessments, or ongoing monitoring tools to assess one's cognitive ability (e.g. impairment or susceptibility to interference) are particularly useful applications of the cognitive assessment tool described herein. It is recognized in the cognitive field that interference in cognitive function created by a multi-tasking environment may severely impact cognitive performance across a range of functions, including perception, attention, and memory. Accordingly, there are many potential populations that would benefit from a new method that specifically aims to measure cognitive function.

Individuals that can benefit from the subject methods and tools include but are not limited to adults, such as aging adults. It is well-known that healthy aging adults have a significant deficit in processing of cognitive interference. Additionally, recent findings show the even young adults can show signs of such a deficit (Int. Pat. No. WO2012/064999A1 by Gazzaley, A.). Therefore, adults about 30 years old, or older, can benefit from the methods of the present disclosure. Declines typically accelerate starting at age 50, and worsen over subsequent decades in a phenomena clinically referred to as "age-related cognitive decline." Such a condition can lead to a more severe ailment known as mild cognitive impairment. If the deficit is identified early cognitive therapeutic steps can be initiated, such as cognitive training. Additionally, prevention measures can be introduced in tasks that require extraction of visual or auditory information while multi-tasking or avoiding distraction, such as driving a car.

For individuals suffering from chronic neurological and psychiatric illness, changes in inhibitory neuron populations, myelination, response slowing, emergent response dis-coordination, degradation of response selectivity in spatial, spectral and temporal detail, and in the degradation of the distinctions between background and target stimuli are very similar to the effects of age-related cognitive decline. Accordingly, individuals of any age with profiles of cognitive impairment that parallel those in aging are target populations for the methods and tools of the present disclosure.

Aside from aging, measuring cognitive impairment can be useful for identifying deficits in others at risk. For example, the disclosed cognitive assessment tool may be useful for identifying cognitive losses that have arisen as a consequence of injury (e. g. traumatic brain injury), medical treatments, chronic illness, or of unknown cause. Such cognitive impairment, age-related or not, can be a contributing factor or manifesting symptom of a variety of conditions, including Alzheimer's disease, Parkinson's disease, Huntington's disease, depression, schizophrenia, dementia (including, but not limited to, AIDS related dementia, vascular dementia, age-related dementia, dementia associated with Lewy bodies, and idiopathic dementia), Pick's disease, cognitive deficits associated with fatigue, multiple sclerosis, post-traumatic stress disorder (PTSD), obsessive-compulsive disorder (OCD), and others. Other cognitive losses can include brain damage attributable to infections pathogens, medical intervention, alcohol, and drugs, among others. Additionally, cognitive decline may result as a secondary symptom from a variety of disease states that are on the surface unrelated to cognition, but which significantly adversely affect anxiety, stress, panic, depression, dysphoria, or malaise. Accordingly, individuals experiencing pain or disease having a significant pain component, insomnia, or potential adverse effects of disease treatment such as general anesthesia, dialysis, chemo therapy, or radiation therapy can also benefit from using the cognitive assessment tool.

Populations that can further benefit from the present cognitive assessment tool further encompass those that suffer from attention deficit disorder (e.g. ADHD). Similarly, cognitive losses can be characterized for developmentally impaired child and adult populations, encompassing general or undiagnosed developmental delays, Sensory Processing Disorder (SPD), and Autism Spectrum Disorder (ASD).

Assessing specifically cognitive abilities related to performing two tasks at once, as described in this disclosure, may be vital for assessing professional abilities. Professions requiring significant multi-tasking include, but are not limited to, athletes, airline pilots, military personnel, doctors, call center employees, teachers, and drivers of vehicles.

Assessing specific cognitive abilities is also useful for people with current or previous substance abuse problems or additions.

Another non-medical population that can benefit from the cognitive assessment tool are school age children. Assessments of cognitive training may be useful in identifying children with special needs or who should be targeted for cognitive training and specific educational programs.

Demonstration of Efficacy

With the goal to assess cognition and related effects in individuals, it can be desirable to experimentally determine the accuracy of a diagnosis. Suitable methods of experimental testing include those types of studies known in the art to test the accuracy of a new cognitive measurement, including pilot studies with humans and clinical trials. These types of experimental tests can be conducted with any group of individuals, and preferably with a group of individuals that represent the target population of the eventual market products. Preferably, the studies are conducted in such a way as to give a strong statistical support to the conclusions.

In one embodiment of such a study, the disclosed methods are used to measure cognition at the same time as another well characterized assessment to compare the two results. This assessment can focus on general cognitive functions, which can pertain to both healthy individuals and individuals that have experienced or are at risk of experiencing cognitive deficits, including clinical patient populations. Such suitable tests include those know in the art to test any specific functions of a range of cognitions in cognitive or behavioral studies, including tests for perceptive abilities, reaction and other motor functions, visual acuity, long-term memory, working memory, short-term memory, logic, decision making and the like.

In another embodiment of an efficacy study, it can be tested if the described cognitive assessment tool captures known cognitive deficits that are associated with aging when tested across a wide range of ages. In such an embodiment other tools can be used in addition to age to correlate with function, such as the cognitive assessments known to one skilled in the art as describe above, or to actual functional activities of daily living. Examples of tests that are specifically constructed or validated to measures such functional outcomes are, Activities of Daily Living for elderly populations, or simple measurements such as the ability to perform a directed task, read, or comprehend conversation; efficiency in a workplace environment; and the like.

In another embodiment of an efficacy study, the cognitive assessment tool can be tested for its ability to capture cognitive changes that are associated with known change agents such as stimulants, depressants, and sleep deprivation. Such a study can also employ known cognitive assessments described previously for comparison to the disclosed methods for assessing cognition.

In another embodiment of an efficacy study, the cognitive assessment tool can be assessed for its ability to capture known cognitive deficits associated with specific disease populations and differentiate severity within a diseased population. In such an embodiment, the disclosed methods for assessing cognition can be compared with other cognitive evaluations and functional measures described above along with tests that measure symptoms or functions relevant to a specific disease or condition. Suitable types of tests include those that objectively measure symptom severity or biomarkers of a disease condition, tests that use subjective clinician or observer measurement of symptom severity, tests that use self-reported perception of a subject's condition, and tests that measure cognitive functions know to be correlate with disease states. Examples of such tests include, but are not limited to assessment scales or surveys such as the Mini Mental State Exam, CANTAB cognitive battery, Test of Variables of Attention (TOVA), Repeatable Battery for the Assessment of Neuropsychological Status, Clinical Global Impression scales relevant to specific conditions, Clinician's Interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities for Daily Living scales, ADHD self-report scale, Positive and Negative Affect Schedule, Depression Anxiety Stress Scales, Quick Inventory of Depressive Symptomatology, and PTSD Checklist; physiological tests that measure internal markers of disease or health such as detection of amyloid beta, cortisol and other stress response markets; and brain imaging studies (for example fMRI, PET, etc.) that assess a condition based on the presence of specific neural signatures.

In another embodiment of efficacy studies, the cognitive assessment tool can be tested for its ability to differentiate between different disease populations that have similar phenotypes. Such a study would use participants with known diagnoses for diseases with similar phenotypes and, potentially individuals with no known disease state related to cognitive function. Such a study could also employ the cognitive, functional, and symptom related tests described previously in this section.

In another embodiment of efficacy studies, the cognitive assessment tool can be employed multiple times for each person all at once or on a fixed schedule in the study to demonstrate the stability of the cognitive measures. Such a study could also give participants cognitive, functional, and symptom related tests described previously in this section at the same time as the disclosed cognitive measurement tool for comparison.

In another embodiment of efficacy studies, the cognitive assessment tool can be employed multiple times for each person all at once or on a fixed schedule while at the same time the user is given a known cognitive enhancing or cognitive impairing treatment to demonstrate the sensitivity of the measure to the known treatment. Such a study could use a neuro-stimulant or caffeine for a cognitive enhancing treatment or alcohol or sleep deprivation for a cognitive impairment treatment. Such a study could also simultaneously with each use of the described cognitive measurement tool employ the cognitive, functional, and symptom related tests described previously in this section.

EXAMPLES

It is understood that the examples and embodiments described herein are for illustrative purposes only and that various modifications or changes in light thereof will be suggested by persons skilled in the art and are to be included within the spirit and purview of this application and scope of the appended claims. All publications, patents, and patent applications cited herein are hereby incorporated by reference in their entirety for all purposes.

Project: EVO—Computational Cognitive Assessment System

We have designed and built an adaptive cognitive assessment system as the underlying software mechanics in a clinical prototype cognitive assessment game entitled "Project: EVO," which is operated by an individual on a mobile tablet or smartphone. The adaptive cognitive assessment system that powers Project: EVO uses the methods of measurements to evaluate the cognitive abilities of the player.

Background of Project: EVO

Project: EVO was built as a mobile video game that can assess the executive function of an individual by measuring inputs the individual gives while performing two tasks concurrently (multi-tasking), in an engaging computer environment. To date, the game has been deployed in multiple clinical studies that use comparisons to standard assessments for cognition, behavioral and symptomatic measurements. Example screenshots from the functional clinical version of Project: EVO are shown in FIG. 3, described above.

Project: EVO presents two types of tasks to an individual: a perceptual reaction task (called "Tapping" in the game) and a visuomotor tracking task (called "Navigation" in the game). The perceptual reaction task requires an individual to respond by tapping on the screen of the mobile tablet/phone when a visual target of interest appears (for example, a green circular fish) but to inhibit their response and not tap the screen when a target that is not of interest appears (for example, a green square-shaped fish or a red circular fish). The visuomotor task requires an individual to "navigate" a visual figure/avatar down a river by subtly tilting the screen of the mobile tablet/phone so as to keep the avatar in the middle of the river. The individual must avoid obstacles that are generated in the avatar's path in order to succeed. The two tasks are based on the basic framework of the multi-tasking paradigm.

Difficulty Levels in Project: EVO

The difficulty level of the tasks the user performs is modified based on user performance. The difficulty of each task for an individual is made to increase as an individual performs the task correctly and the difficulty decreases when an individual fails to perform a task correctly. For the reaction task performing the task correctly is considered responding in the proper amount of time to the targets of interest and not responding to targets that are not of interest. Perform the reaction task incorrectly is the opposite, responding to a target that is not of interest or not responding to targets of interest in the allotted amount of time. The difficulty of the reaction task is modified by increasing or decreasing the response time allowed when each target is presented. The game-level for the reaction tasks is determined by the reaction time window presented to the participant. The navigation task is considered to be performed correctly when the user avoids the walls and objects in the avatar's path. Allowing the avatar to collide with walls and objects is considered incorrectly performing the navigation task. The difficulty level for an individual of the navigation task is modified by changing the speed of the avatar moving down the path. The game-level for the navigation task is determined by the speed of the avatar moving down the path. Project: EVO adapts the difficulty level of both tasks in real-time, in order to keep a user challenged and determine the threshold of performance possible by the user. Therefore, the individual's performance on the previous events of gameplay determines the exact difficulty of the next event, and the aggregate performance over an extended period of time generally determines the average difficulty level that an individual may be experience at any one time.

"Worlds" of Project: EVO

The current version of the Project: EVO assessment tool was designed with four different "Worlds" the tasks take place in. For each of the different worlds there are different graphics, different color schemes, and slightly different perceptual reaction tasks. In some cases all of the worlds are used in an assessment and in other cases, only one of the worlds is used as an assessment.

Playing Project: EVO Assessment

Project: EVO is set up so that the game can be played one time or multiple times over a set time period; for example, once a day for four days. The player starts the assessment process by practicing the two task for a short period of time, 4-12 minutes. A player is motivated to play to their maximal ability by visual and auditory feedback to every targeting event and incorrect navigation events. In some cases, the player is also rewarded for performing the tasks correctly with "points" that can be used to purchase avatars. After this warm-up period the player starts an evaluation phase. The player completes each task by itself (single-tasking) and both tasks simultaneously (multi-tasking) until a threshold level of performance is reached.

Data Recorded in Project: EVO Assessment

While the player is immersed in the multi-tasking phase of the game, the user's performance measures are recorded. Specifically, the navigation level, the tapping level, the reaction time to stimuli in the perceptual reaction task, and whether a user response correctly to an interference stimuli by tapping or correctly to a distractor stimuli by not tapping the touch screen. These specific data points are used to calculate other measures that represent cognitive measures, such as the threshold performance levels, mean performance level, variation in performance levels, mean reaction time, variation in reaction time, and other complex and composite cognitive function variables.

Training Program with Project: EVO

Sometimes, the Project: EVO assessment tool is accompanied by a Project: EVO personalized training program with adaptive rewards (Int. Pat. No. WO2012/064999A1 by Gazzaley, A.; U.S. Pat. Appl. No. 62/001,141 by Martucci, Piper, Omernick, Gazzaley, Elenko, and Karanam). The personalized training program involves practicing the multi-tasking phase of the assessment with encouragement and rewards for performing both tasks well. The difficulty of the adaptive reward program and the gates that allow a user to progress to the next world is set by the Project: EVO Assessment results. Data for assessment can also be generated during this training phase.

Pilot Study: Multitasking System Detects Known Cognitive Decline in Aging

We conducted a study using our assessment tool for a group of older adults (between 60 and 75 years old, n=15) and a group of younger adults (ages between 20 and 30 years old, n=19). This study was conducted with an academic partner trained in cognitive assessment methods. Participants had no other known cognitive impairment and had no symptoms of depression. The older adults were also required to have a Mini-Mental State Exam score great than or equal to 27.

Participants in the study were given an evaluation in different EVO worlds within the game. The participants then participated in the Project: EVO cognitive training program, which includes taking the evaluation at least two more times within each world. This process was repeated for at least 3 worlds. Participants were given the worlds in a random order. The participants played at most 7 rounds of the Project: EVO training or assessment per day for 28 days. The initial evaluation was done in the lab setting under the supervision of the researcher. All the remaining sessions were played at home with no guidance or interference from the research team.

The results present are from just one of the worlds within the Project: EVO game. FIG. 4 presents the results of the assessment studies. There was significant difference ($p<0.05$) between the older adults and the younger adults for the mean reaction time to stimuli (FIG. 4.A) and the standard deviation of the reaction time (FIG. 4.B) while the participants are in a multi-tasking environment. Our cognitive measurement tool was able to show the cognitive decline that is known to be present in older adults.

Pilot Study: Multi-Tasking Measures Differentiate Populations Better than Other Cognitive Tests and Single-Tasking Measures The embodiment described in this disclose would prove greater than state of the art cognitive measures if it were able to differentiate a population that has a well-established risk for neurodevelopmental disabilities including autism, those with deletions and duplications at chromosome 16p.11.2 BP4-BP5, from neurotypical age-matched siblings better than other cognitive tests. Potentially, this could be tested at an annual meeting for families of children with this specific disorder.

In such a study, both the 16p.11 carrier children and their siblings would play a Project: EVO assessment along with Motor Speed and Symbol Digit tests that assess basic motor and processing speed abilities and Flanker and Visual Search tests that assess attention based processing in the presence of a distraction.

The study would prove successful if Project: EVO multi-tasking measures such as game level threshold and reaction time while multi-tasking were able to differentiate between the carrier children and the neurotypical children better than the traditional cognitive tests that are not multi-tasking.

Pilot Study: Multitasking Measurements May Enable Unique Disease Signatures

The disclosed method for measuring cognitive function would be useful above the state of the art if the multi-tasking cognitive measures are able to differentiate between different cognitively impaired populations, such as Sensory Processing Disorder, Autism Spectrum Disorder, and Attention Deficit Hyperactivity Disorder (ADHD). If data from these different populations, which could potentially be collected through different clinical research protocols, demonstrate that these populations are differentiated from the neurotypical cohorts through distinct patterns of multi-task measures, this tool would be clinically useful. These patterns in the measurements are unique disease signatures, showing the ability our cognitive measurement tool to differentiate between different cognitively impaired populations, some with similar cognitive phenotypes with as Autism Spectrum Disorder and Sensory Processing Disorder.

Pilot Study: Stability of Multi-Tasking Performance Measures Over Time

The tool described in this disclosure would be clinically useful if the multi-tasking cognitive measures are reliable and stable over time and multiple uses of the measurement tool. The EVO Assessment tool can be played by a user on varying schedules. Such schedules include using the tool once per day, using the tool multiple times spread out over the day, using the tool a few times per week, and using the tool multiple times per week. Within a specific user or within a group of users on a similar schedule, the stability can be evaluated by calculating the Interclass Correlation Coefficient (ICC) ICC scores greater than 0.70 indicate good reliability. The ICC can be computed for both neurotypical populations and populations with known illness or cognitive impairment.

Pilot Study: Sensitivity of Multi-Tasking Cognitive Measurements to Pharmacologic Agents or Circadian Rhythm The tool described in the disclosure would be considered a sensitive cognitive measurement if the measurement changes outside of expected variation when the person using the tool has taken a cognitive enhancing agent (such as methylphenidate) or a cognitively detrimental agent (such as triazolam). Sensitivity to these agents could be tested by having participants take a placebo, methylphenidate, and triazolam in a random and unknown order. If the performance on the multi-tasking test changes from before to after the drugs, the tool is sensitive to cognitive function changes.

Additionally, without using cognitive agents, there is known subtle increase and decrease in cognitive function due to circadian rhythm and time awake. If the multi-tasking cognitive measures described in this disclosure are sensitive to such circadian rhythms or extended periods of time awake, as defined by the ability to detect such a state statistically, it would be a marker of sensitive cognitive measurement.

Measurement of Multi-Tasking Performance During Commercial Video Game Play as a Cognitive Assessment The described cognitive measurement methods are embodied by the measurement of user inputs while the user is engaged in multi-tasking in a commercially available video game on a gaming console. During the video game the user explores a "world" created in the video game to look for enemy soldiers. When the user identifies an enemy soldier the user attempts to shoot the soldier. At times, the user can be engaged in both moving around the world and shooting a target (the enemy soldier). When the user is engaged in both of these tasks, the user is multi-tasking. Data from user inputs are extracted for any moment in which the user is engaged in multi-tasking during a session of game play. The user input data is analyzed by a computer device to determine the accuracy of the targeting, accuracy of targeting under increased difficult (speed of a moving target), the pace at which the user is moving, the number of times a user creates an error in the navigation of the video game world (e.g. running into an obstacle), the pattern of movement while navigating the world (e.g. the number of times the avatar needs to back track), and other performance measures. Standard statistical summary methods are also computed to represent cognitive measures. Data regarding the user's performance is outputted by the computer device as an indications of the user's current cognitive assessment. After a performance baseline is established, passive monitoring in this engage manner of video game play can be used to assess the level of sleep deprivation for healthy individuals or to monitor changes in cognitive function after a medical intervention such as stimulant therapy for a young adult with ADHD.

Measurement of Multi-Tasking Performance During Written Communications as a Cognitive Assessment The disclosed cognitive assessment tool may be embodied by the measurement of keyboard user inputs on a laptop or desktop computer while a user is engaged in written communication and instant messaging. During the use of a computer for recreational or work related purposes, a user is often engaged in writing a letter, report, or email while at the same time responding to instant messages. The instances in which a user is actively writing in a word document or email, determined as the time within 30 seconds of active typing, and actively responding to instant messaging, determined as the time when a user engages in an instant message communication window and types a response on the keyboard, the user is determined to be multi-tasking. During periods of multi-tasking, the user inputs to the computer device are extracted. This data is used to evaluate the typing speed, typing accuracy (as determined by the number of misspelled words, the number of times a user must delete text, or a composite of the two), the processing time (time with an active instant messaging, email, or document window activated before typing is started or percent time with an active instant messaging, email, or document window activated during which no typing is occurring), reaction time to the alert that a new instant message has been received, and other performance measures. These data are also be used to create complex measures of cognitive function. Data regarding the user's performance is outputted by the computer device as an indication of a user's current cognitive assessment. After a performance baseline is established, the cognitive assessment tool is used by employers to establish an ideal workplace for an employee and used by schools as a passive screen to identify students who may need cognitive training or further cognitive testing for attention or sensory disorders.

Aspects of the present disclosed methods are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 5:
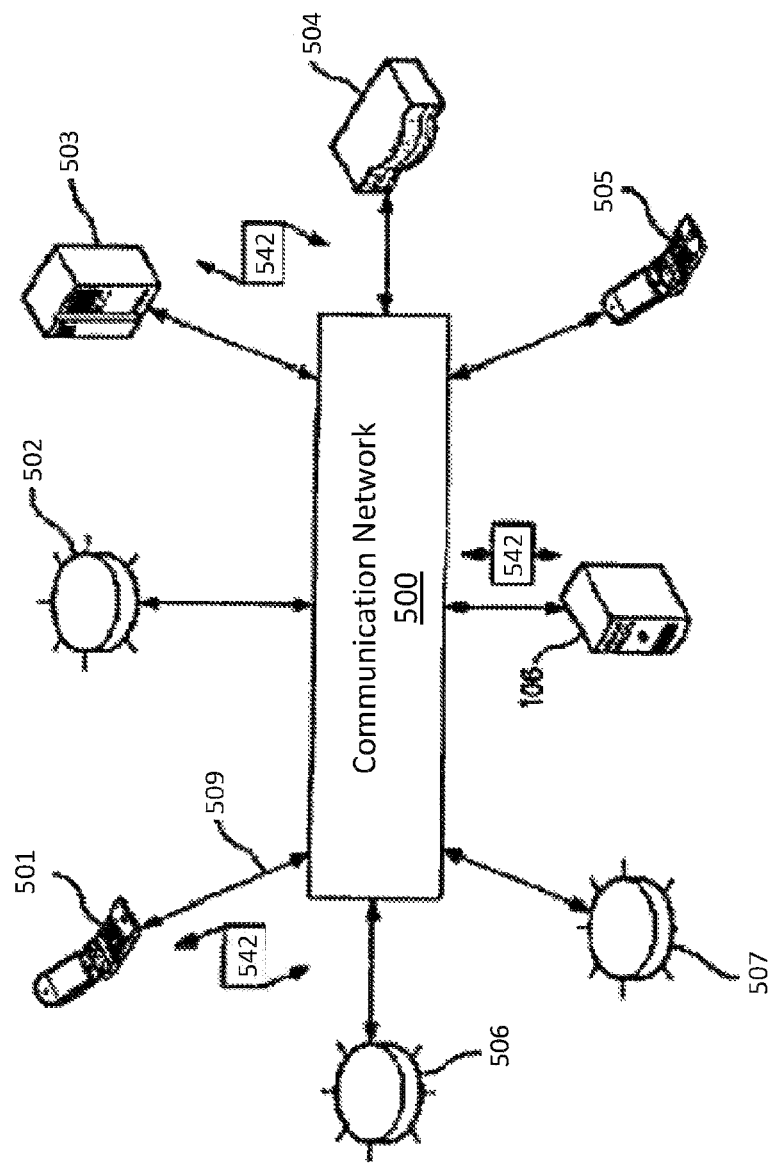
FIG. 5 depicts an exemplary computer processing system for use in implementing an exemplary cognitive assessment tool.

FIG. 5 is a schematic block diagrams of an example network 500 and computing devices that may be used (or components thereof) with one or more embodiments described herein, e.g., as one of the nodes shown in the network 500. In one embodiment, a computer processing system for assessing cognitive abilities may be a single mobile device 501. For example, the mobile device 501 may present the tasks to the individual user, receive responses from the individual, determine that the tasks are performed by the individual (the user is multi-tasking), determine performance measures using the responses, computing a cognitive measure using the performance measures, and output a cognitive ability assessment. In another embodiment, a computer processing system for assessing cognitive condition may be a distributed computing system including several processing units. For example, a mobile device 503 may present the tasks to the individual, receive responses from the individual, and transmit the responses through communication network 500 to a server 506 for subsequent processing. The server 506 may receive the response, determine that the tasks are performed by the individual, determine performance measures using the responses, compute a cognitive measure using the performance measures, and output a cognitive ability assessment to the mobile device 503 for display. In another embodiment, the performance measures may be determined by the mobile device 503 rather than by the server 506. Other division of labor among distributed processing components (which may be more than 2) are within the prevue of one of ordinary skill in the art.

Figure 6:
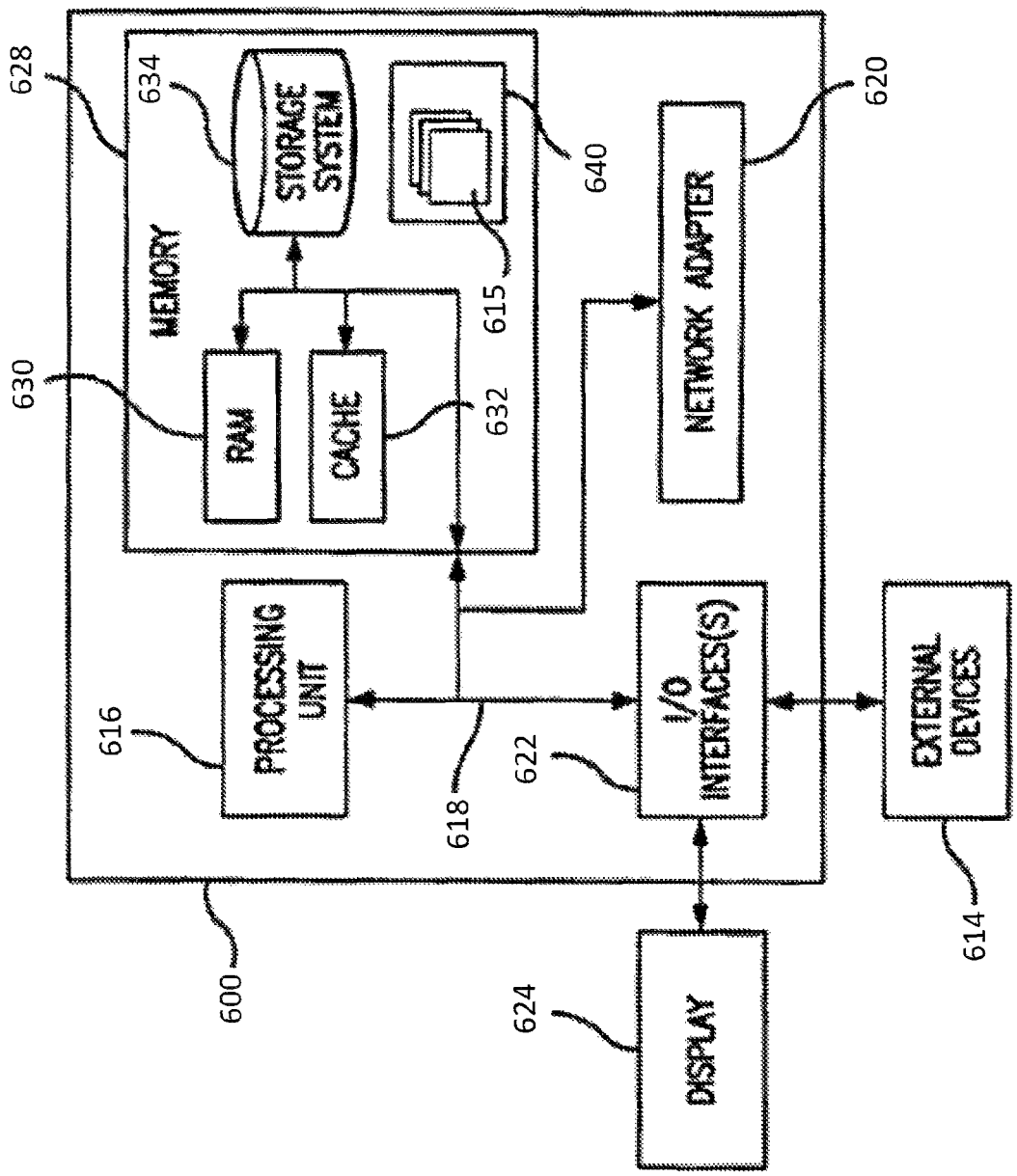
FIG. 6 depicts an exemplary computer processing system for use in implementing an exemplary cognitive assessment tool.

FIG. 6 is a block diagram of an exemplary computer processing system or computing device 600. The depicted system is only one example of a suitable system and is not intended to suggest any limitation as to the scope of use or functionality of embodiments of the invention described herein. In one embodiment, the system 600 includes a processing unit 616 (e.g., a CPU, GPU, etc.). The processing unit 616 may access and write to memory 628 through bus 618. Memory 628 may include, e.g., Random Access Memory (RAM) 630, cache 632, and storage system 634 (e.g., hard drive, flash drive, DVD drive, etc.). Within memory 628, a file structure 640 may be implemented to store and provide access to files and data 615. The processing unit 616 may also be in communication with a network adapter 620 that enables the system 600 to communicate with other devices in a network. Examples of network adapters 620 include, e.g., Ethernet adapters, Wi-Fi wireless adapters, and cellular network adapters. Further, the processing unit 616 may output and receive data through an input/output interface (I/O interface) 622, which may enable system 600 to output data to or receive data from external devices (e.g., mouse, keyboard, CD drive, etc.) 614 and displays (e.g., monitors, touch screen, etc.) 624.

With certain illustrated embodiments described above, it is to be appreciated that various non-limiting embodiments described herein may be used separately, combined or selectively combined for specific applications. Further, some of the various features of the above non-limiting embodiments may be used without the corresponding use of other described features. The foregoing description should therefore be considered as merely illustrative of the principles, teachings and exemplary embodiments of this invention, and not in limitation thereof.

It is to be understood that the above-described arrangements are only illustrative of the application of the principles of the illustrated embodiments. Numerous modifications and alternative arrangements may be devised by those skilled in the art without departing from the scope of the illustrated embodiments, and the appended claims are intended to cover such modifications and arrangements.

What is claimed is:

1. A computer-implemented method comprising:
receiving, by a computer processing system, a first plurality of responses by an individual to a first task, the first task comprising a first stimuli configured to evoke the first plurality of responses from the individual over a period of time;
receiving, by the computer processing system, a second plurality of responses by the individual to a second task, the second task comprising a second stimuli configured to evoke the second plurality of responses from the individual over the period of time, wherein the second stimuli are presented simultaneously with at least some of the first stimuli;
computing, by the computer processing system, a cognitive measure using a combination of one or both of the first plurality of responses and the second plurality of responses and external information, wherein computing the cognitive measure comprises:
(i) determining at least one performance measure using one or both of the first plurality of responses and the second plurality of responses, the at least one performance measure being associated with one or more cognitive functions associated with one or more specific diseases or disease states,
(ii) comparing the at least one performance measure to the external information, the external information comprising one or more performance measure of individuals with known cognitive conditions associated with the one or more specific diseases or disease states, and
(iii) applying a computer data model comprising at least one machine learning technique to the performance measures, wherein the at least one machine learning technique is configured to analyze one or more stimulus-response patterns from the first plurality of responses and the second plurality of responses to compute a predictive measure for the one or more specific diseases or disease states; and
outputting, by the computer processing system, a cognitive assessment for the individual based on the cognitive measure,
wherein one or both of the first plurality of responses and the second plurality of responses (i) comprise at least one of motion by the individual or physiological input from the individual, and (ii) are detected using one or more sensors, the sensors being selected from the group consisting of an accelerometer, a gyroscope, and a physiological sensor.

2. The computer-implemented method of claim 1, wherein the first task is a visuomotor task, the first stimuli include a navigation path, and the first plurality of responses include continuous inputs.

3. The computer-implemented method of claim 1, wherein the second task is a reaction task, the second stimuli include target stimuli that require responses from the individual, and the second plurality of responses include inputs reacting to the target stimuli.

4. The computer-implemented method of claim 3 wherein the second stimuli include distractor stimuli that require no response from the individual.

5. The computer-implemented method of claim 1 wherein computing the cognitive measure comprises computing one or more of a hit rate, false alarm rate, correct response rate, and miss rate.

6. The computer-implemented method of claim 1 further comprising
modifying, during the period of time, a difficulty level of the first task or the second task based on performance measures.

7. The computer-implemented method of claim 6 wherein the difficulty level is selected from the group consisting of: allowable reaction time window for reacting to stimuli, navigation speed, number of obstacles, size of obstacles, frequency of turns in a navigation path, and turning radiuses of turns in a navigation path.

8. The computer-implemented method of claim 1 further comprising:
modifying, during the period of time, a first difficulty level of the first task based on performance measures of one or both of the first plurality of responses and the second plurality of responses; and
modifying, during the period of time, a second difficulty level of the second task based on performance measures of one or both of the first plurality of responses and the second plurality of responses.

9. The computer-implemented method of claim 8 wherein the cognitive measure is computed using one or both of the first difficulty level modifications and the second difficulty level modifications.

10. A computer-implemented system comprising:
one or more processors; and
a non-transitory computer-readable memory comprising instructions stored thereon that, when executed, cause the one or more processors to execute operations comprising:
receiving a first plurality of responses by an individual to a first task, the first task comprising a first stimuli configured to evoke the first plurality of responses from the individual over a period of time;
receiving a second plurality of responses by the individual to a second task, the second task comprising a second stimuli configured to evoke the second plurality of responses from the individual over the period of time, wherein the second stimuli are presented simultaneously with at least some of the first stimuli;
computing a cognitive measure using a combination of one or both of the first plurality of responses and the second plurality of responses and external information, wherein computing the cognitive measure comprises:
(i) determining at least one performance measure using one or both of the first plurality of responses and the second plurality of responses, the at least one performance measure being associated with the one or more cognitive functions associated with one or more specific diseases or disease states,
(ii) comparing the at least one performance measure to the external information, the external information comprising one or more performance measure of individuals with known cognitive conditions associated with the one or more specific diseases or disease states, and
(iii) applying a computer data model comprising at least one machine learning technique to the performance measures, wherein the at least one machine learning technique is configured to analyze one or more stimulus-response patterns from the first plurality of responses and the second plurality of responses to compute a predictive measure for the one or more specific diseases or disease states; and
outputting a cognitive assessment for the individual based on the cognitive measure,
wherein one or both of the first plurality of responses and the second plurality of responses (i) comprise at least one of motion by the individual or physiological input from the individual, and (ii) are detected using one or more sensors, the sensors being selected from the group consisting of an accelerometer, a gyroscope, and a physiological sensor.

11. The computer-implemented system of claim 10 wherein the first task is a visuomotor task, the first stimuli include a navigation path, and the first plurality of responses include continuous inputs.

12. The computer-implemented system of claim 11 wherein the operations further comprise modifying, during the period of time, a second difficulty level of the second task based on performance measures of one or both of the first plurality of responses and the second plurality of responses.

13. The computer-implemented system of claim 12 wherein the first difficulty level and the second difficulty level are modified in real-time during the period of time.

14. The computer-implemented system of claim 13 wherein the cognitive measure is computed using one or both of the first difficulty level modifications and the second difficulty level modifications.

15. The computer-implemented system of claim 10 wherein the second task is a reaction task, the second stimuli include target stimuli that require responses from the individual, and the second plurality of responses include inputs reacting to the target stimuli.

16. The computer-implemented system of claim 15 wherein the second stimuli include distractor stimuli that require no response from the individual.

17. The computer-implemented system of claim 10 wherein computing the cognitive measure comprises computing one or more of a hit rate, false alarm rate, correct response rate, and miss rate.

18. The computer-implemented system of claim 10 wherein computing the cognitive measure includes applying a signal detection technique selected from the group consisting of: sensitivity index, receiver operating characteristics (ROC), and bias.

19. The computer-implemented system of claim 10 wherein the operations further comprise modifying, during the period of time, a first difficulty level of the first task based on performance measures of one or both of the first plurality of responses and the second plurality of responses.

20. A non-transitory computer-readable medium encoded with instructions thereon that, when executed by a computer processing system, cause the computer processing system to perform one or more operations, the one or more operations comprising:
receiving a first plurality of responses by an individual to a first task, the first task comprising a first stimuli configured to evoke the first plurality of responses from the individual over a period of time;
receiving a second plurality of responses by the individual to a second task, the second task comprising a second stimuli configured to evoke the second plurality of responses from the individual over the period of time, wherein the second stimuli are presented simultaneously with at least some of the first stimuli;
computing a cognitive measure using a combination of one or both of the first plurality of responses and the second plurality of responses and external information, wherein computing the cognitive measure comprises:
(i) determining at least one performance measure using one or both of the first plurality of responses and the second plurality of responses, the at least one performance measure being associated with the one or more cognitive functions associated with one or more specific diseases or disease states, (ii) comparing the at least one performance measure to the external information, the external information comprising one or more performance measure of individuals with known cognitive conditions associated with the one or more specific diseases or disease states, and (iii) applying a computer data model comprising at least one machine learning technique to the performance measures, wherein the at least one machine learning technique is configured to analyze one or more stimulus-response patterns from the first plurality of responses and the second plurality of responses to compute a predictive measure for the one or more specific diseases or disease states; and outputting a cognitive assessment for the individual based on the cognitive measure, wherein one or both of the first plurality of responses and the second plurality of responses (i) comprise at least one of motion by the individual or physiological input from the individual, and (ii) are detected using one or more sensors, the sensors being selected from the group consisting of an accelerometer, a gyroscope, and a physiological sensor.

* * * * *